(12) United States Patent
Herlyn

(10) Patent No.: US 6,528,307 B1
(45) Date of Patent: Mar. 4, 2003

(54) CYTOLYTIC T-CELL CLONES AGAINST COLORECTAL CARCINOMA

(75) Inventor: Dorothee Herlyn, Wynnewood, PA (US)

(73) Assignee: The Wistar Institute of Anatomy and Biology, Philadelphia, PA (US)

(*) Notice: Subject to any disclaimer, the term of this patent is extended or adjusted under 35 U.S.C. 154(b) by 0 days.

(21) Appl. No.: 09/403,310

(22) PCT Filed: Apr. 23, 1998

(86) PCT No.: PCT/US98/08266

§ 371 (c)(1),
(2), (4) Date: Oct. 18, 1999

(87) PCT Pub. No.: WO98/49270

PCT Pub. Date: Nov. 5, 1998

Related U.S. Application Data

(60) Provisional application No. 60/044,890, filed on Apr. 25, 1997.

(51) Int. Cl.⁷ ................................................. C12N 5/08
(52) U.S. Cl. .................................................... 435/372.3
(58) Field of Search ...................................... 435/372.3

(56) References Cited

U.S. PATENT DOCUMENTS 5,550,214 A      8/1996   Eberlein ..................... 530/328
5,874,304 A   *  2/1999   Ohno et al.

OTHER PUBLICATIONS

The Merck Manual 16th ed Boekow, ad., p. 852–854, 1992.*
Genes III Lewin, p. 723, 1987.*
S. Somers et al., "Isolation and Expansion of Lymphoctes from Gastrointestinal Tumour Tissue", *Surg. Oncol.*, 2:283–291 (Oct. 1993).
A. Houghton, "On Course for a Cancer Vaccine", *The Lancet*, 345: 1384–1385 (Jun. 3, 1995).
Y. Kawakami et al., "Section 3.1 Genes Coding for Tumor Antigens Recognized by T Lymphocytes", *Biologic Therapy of Cancer*, 2nd ed., V.T. De Vita, S. Hellman, and S. Rosenberg, eds.; Philadelphia: J. Lippincott, pp 53–63 (1995).
Y. Kawakami et al., "Recognition of Multiple Epitopes in the Human Melanoma Antigen gp100 by Tumor–Infiltrating T Lymphocytes Associated with In vivo Tumor Regression", *J. Immunol.*, 154: 3961–3968 (Apr. 15, 1995).
Y. Hayashi et al., "Induction of CD4⁺ Cytotoxic Cells by Sensitization with Allogeneic Melanomas Bearing Shared or Cross–Reactive HLA–A" *Cell, Immunol.*, 139:411–425 (Feb. 1992).
L LeMay et al., "Detection of Melanoma–Reactive CD4⁺ HLA–Class I–Restricted Cytotoxic T Cell Clones with Long–Term Assay and Pretreatment of Targets with Interferon–γ", *Cancer Immunol. Immunother.*, 38:187–194 (Aug. 1993).

D. Kharkevitch et al., "Characterization of Autologous Tumor–Specific T–Helper 2 Cells in Tumor–Infiltrating Lymphocytes from a Patient with Metastatic Melanoma", *Int. J. Cancer*, 58:317–323 (Aug. 1, 1994).
T. Morisaki et al., "Characterization and Augmentation of CD4⁺ Cytotoxic T Cell Lines Against Melanoma", *Cancer Immunol Immunother.*, 39:172–189 (Sep. 1994).
B. Patel et al., "An Analysis of Autologous T–Cell Anti–Tumour Responses in Colon–Carcinoma Patients Following Active Specific Immunization (ASI)", *Int. J. Cancer*, 51:878–885 (Jul. 30, 1992).
S. Hom et al., "Specific Immune Recognition of Autologous Tumor by Lymphocytes Infiltrating colon Carcinomas: Analysis by Cytokine Secretion", *Cancer Immunol. Immunother.*, 36: 1–8 (1993).
J. Ransom et al., "Identification of Colon–tumor Associated Antigens by T–Cell Lines Derived From Tumor–Infiltrating Lymphocytes From Patients Immunized with an Autologous Tumor–Cell/Bacillus Calmette–Guérin Vaccine", *Int. J. Cancer*, 54:734–740 (Jul. 9, 1993).
W. Mulder et al., "Culture of Tumour–Infiltrating Lymphocytes from Melanoma and Colon Carcinoma: Removal of Tumour Cells Does not Affect Tumour–Specificity", *Cancer Immunol. Immunother.*, 41:293–301 (Nov. 1995).
B. Fossum et al., "p21–ras–Peptide–Specifice T–Cell Responses in a Patient with Colorectal Cancer. CD4⁺ and CD8⁺ T Cells Recognize a Peptide Corresponding to a Common Mutation (13 Gly→Asp)", *Int. J. Cancer*, 56:40–45 (Jan. 2, 1994).
B. Fossum et al., "CD8⁺ T Cells From a Patient with Colon Carcinoma, Specific for a Mutant p21–Ras–Derived Peptide (GLY13→ASP), are Cytotoxic Towards a Carcinoma Cell Line Harbouring the Same Mutation", *Cancer Immuno. Immunother.*, 40:165–172 (Mar. 1995).
K. Tsang et al., "Generation of human Cytotoxic T Cells Specific for Human Carcinoembryonic Antigen Epitopes From Patients Immunized with Recombinant Vaccinia–CEA Vaccine", *J. Natl. Cancer Inst.*, 87:982–990 (Jul. 5, 1995).
D. Guerry et al., "HLA–DR Histocompatibility Leukocyte Antigens Permit Cultured Human Melanoma Cells from Early but not Advanced Disease to Stimulate Autologous Lymphocytes", *J. Clin Invest.*, 73:267–271 (Jan. 1984).
D. Guerry et al., "Interferon–γ Regulates the T Cell Response to Precursor NEVI and Biologically Early Melanoma", *J. Immunol.*, 139:305–312 (Jul. 1, 1987).

(List continued on next page.)

*Primary Examiner*—Patrick J. Nolan
*Assistant Examiner*—Gerald R. Ewoldt
(74) *Attorney, Agent, or Firm*—Howson and Howson

(57) ABSTRACT

Two stable cytolytic T lymphocyte cell lines and a clone are established from two primary colorectal carcinoma patients. A method for generating stable anti-colorectal carcinoma CTL clones and cell lines includes the step of stimulating the lymphocytes of a patient with minimal or no clinical evidence of colorectal carcinoma in culture with irradiated autologous primary colorectal carcinoma tumor cells, interleukin-2, and either autologous lymphocytes or autologous EBV-B cells.

2 Claims, 9 Drawing Sheets

OTHER PUBLICATIONS

J. Travis, "Do Tumor–Altered T Cells Depress Immune Responses?", *Science*, 258: 1732–1733 (Dec. 11, 1992).

C. Loeffler et al., "Immunoregulation in Cancer–Bearing Hosts", *J. Immunol.*, 149:949–956 (Aug. 1, 1992).

H. Mizoguchi et al., "Alterations in Signal Transduction Molecules in T Lymphocytes from tumor–Bearing Mice", *Science*, 258:1795–1798 (Dec. 11, 1992).

H. Nakagomi et al., "Decreased Expression of the Signal–Transducing ζ Chains in tumor–Infiltrating T–Cells and NK Cells of Patients with Colorectal Carcinoma", *Cancer Res.*, 53:5610–5612 (1993).

S. Salvadori et al., "Abnormal Signal Tranduction by T Cells of Mice with Parental Tumors is not Seen in Mice Bearing IL–2–Secreting Tumors", *J. Immunol.*, 153:5176–5182 (Dec. 1, 1994).

J.H. Finke et al., "Loss of T–Cell Receptor $f$ Chain and $p56^{lck}$ in T–cells Infiltrating Human Renal Cell Carcinoma", *Cancer Res.* 53:5613–5616 (Dec. 1, 1993).

C. Cordon–Cardo et al., "Expression of HLA–A,B,C Antigens on Primary and Metastatic Tumor Cell Populations of Human Carcinomas", *Cancer Res.*, 51:6372–6380 (Dec. 1, 1991).

A. Csiba et al., "Distribution of Histocompatibility and Leucocyte Differentiation Antigens in Normal Human Colon and in Benign and Malignant Colonic neoplasms", *Br. J. Cancer*, 50:699–709 (Nov. 1984).

F. Momburg et al., "Loss of HLA–A,B,C and De Novo Expression of HLA–D in Colorectal Cancer", *Int. J. Cancer*, 37:179–284 (Feb. 15, 1986).

L. Jacob et al., "Cytotoxic T–Cell Clone Against Rectal Carcinoma Induced by Stimulation of a Patients Peripheral Blood Mononuclear Cells with Autologous Cultured Tumor Cells", *Int. J. Cancer*, 71:325–332 (May 2, 1997).

R. Gohara et al., "Histocompatibility Leukocyte Antigen–A2402–Restricted Cytotoxic T Lymphocytes Recognizing Adenocarcinoma in Tumor–Infiltrating Lymphocytes of Patients with Colon Cancer", *Jpn. J. Cancer Res.*, 88:198–204 (Feb. 1997).

H. Nagaoka et al., "Establishment of Cytotoxic CD4+ T Cell Clones from Cancer Patients Treated by Local Immunotherapy", *Biotherapy*, 5:241–250 (1992).

K. Tsang et al., "Phenotypic Stability of a Cytotoxic T–Cell Line Directed Against an Immunodominant Epitope of Human Carcinoembryonic Antigen", *Clin. Cancer Res.*, 3:2439–2449 (Dec. 1993).

\* cited by examiner

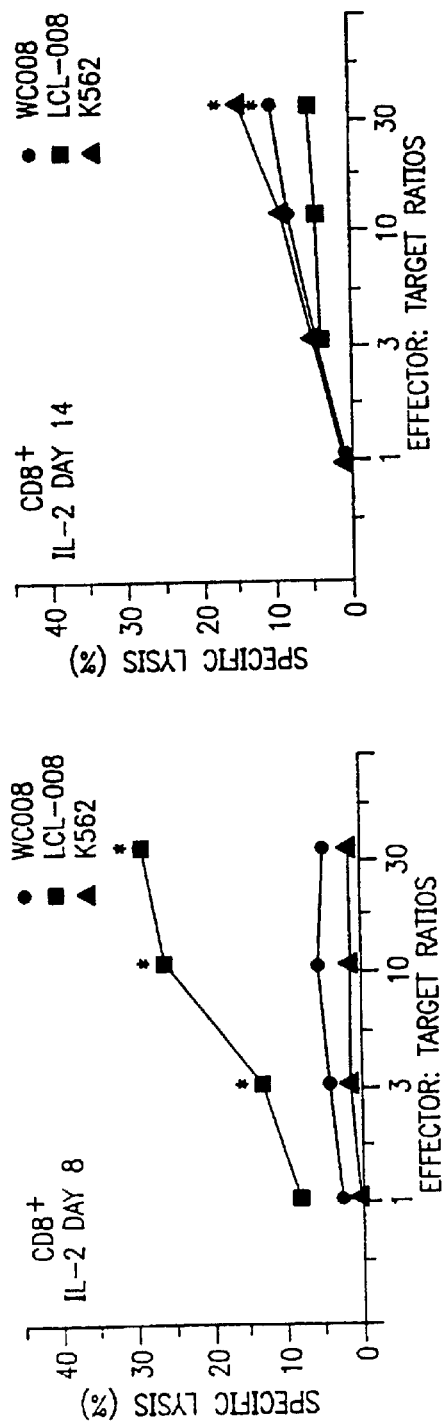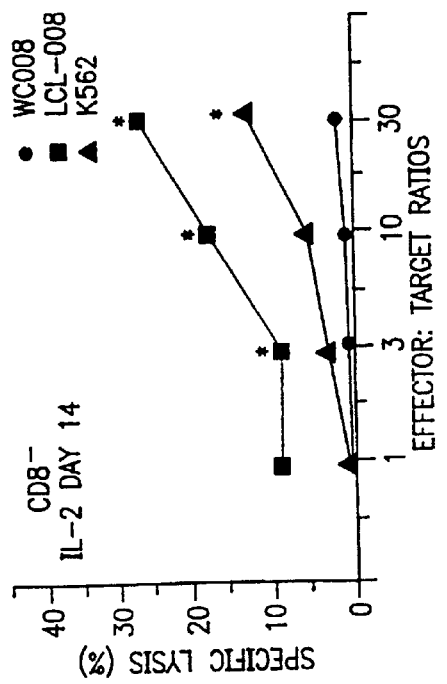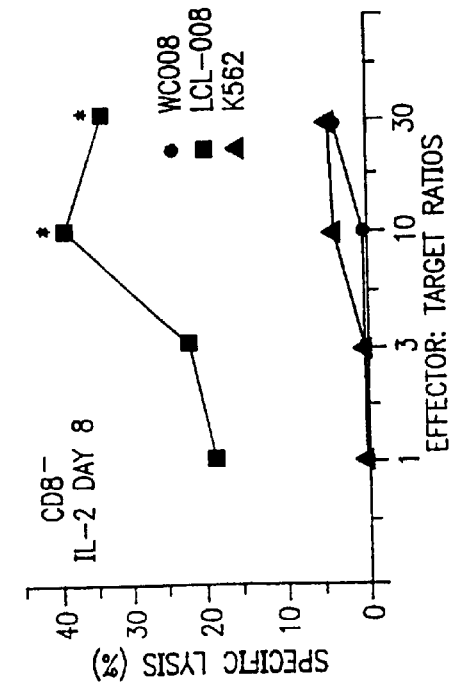

CYTOLYTIC T-CELL CLONES AGAINST COLORECTAL CARCINOMA

CROSS-REFERENCE TO RELATED APPLICATIONS

This is a 371 of PCT/US98/08266, which claims the benefit of the priority of U.S. Patent Application No. 60/044,890, filed Apr. 25, 1997.

This invention has been supported by grants from the National Institutes of Health, Grant No. CA-10815. The United States government has certain rights in this invention.

FIELD OF THE INVENTION

The present invention relates generally to cytolytic T lymphocyte clones derived from colorectal cancers and methods of use thereof in therapy, assays and drug screening.

BACKGROUND OF THE INVENTION

Immunotherapy has been proposed as an alternative and/or complementary approach to conventional chemotherapy and radiation therapy in the treatment of certain cancers. In light of the important role that cellular immunity may play in the control of cancer [A. Houghton, *The Lancet,* 345:1384–1385 (1995)], approaches to the specific modulation of patients' T-cell responses need to be developed.

Perhaps the most promising immunotherapy involves adoptive transfer of cytolytic T lymphocytes (CTLs) and/or active immunization with CTL-defined antigens. Peptides or cloned antigens recognized by patients' lymphocytes may provide effective cancer vaccines. For example, cytolytic T lymphocytes (CTL) induced in melanoma patients' lymphocytes by stimulation with autologous tumor cells provided the basis for the development of antigen- and peptide-derived vaccines against this tumor type [Y. Kawakami et al, in *Biologic Therapy of Cancer,* 2nd edition, pp. 53–64, eds. V. T. DeVita, S. Heliman, and S. Rosenberg, Philadelphia: J. Lippincott (1995) (Kawakami III)]. Kawakami, Y., et al., *J. Immunol.,* 154: 3961–3968 (1995) (Kawakami II) demonstrated that adoptive transfer of CD8+ CTL against melanoma-associated antigen gp 100 induced tumor regression in the autologous patient. The CTLs had been induced by stimulating the patient's tumor-infiltrating lymphocytes with autologous, fresh tumor cells.

Descriptions of known CD4+ CTL which are able to lyse autologous cells in a human leukocyte antigen (HLA) class I dependent manner [Hayashi, Y., et al., *Cell Immunol.,* 139 411–425 (1992); L. LeMay et al, *Cancer Immunol. Immunother.,* 37:187–194 (1993); D. Kharkevitch et al, *Int. J. Cancer,* 58:317–323 (1994); T. Morisaki et al, *Cancer Immunol. Immunother.,* 39:172–178 (1994)], have reported that target cell lysis by the CD4+ CTL was slow (requiring overnight incubation of CTL and targets).

Colorectal carcinoma (CRC) is, after lung carcinoma, the most common type of cancer in the United States. However, attempts to establish CTL against colorectal carcinoma (CRC) by stimulating CRC patients' lymphocytes with autologous tumor cells have been unsuccessful so far. The T cells induced in CRC patients by stimulation of the patients' lymphocytes with autologous tumors have usually been non-cytolytic [B. Patel et al, *Int. J. Cancer,* 51:878–885 (1992); S. Horn et al, *Cancer Immunol. Immunother.,* 36:1–8 (1993); J. Ransom et al, *Int. J. Cancer,* 54:734–740 (1993); S. Somers et al, *Surg. Oncol.,* 2:283–291 (1993); and W. Mulder et al, *Cancer Immunol. Immunother.,* 41:293–301 (1995)].

In two studies, CTL induction by specific peptide stimulation in CRC patients' lymphocytes was demonstrated. In one study, induction of CTL against CRC required specific in vitro stimulation of the lymphocytes with a defined peptide, mutated p21 ras [B. Fossum et al, *Int. J. Cancer,* 56:40–45 (1994) (Fossum I) and B. Fossum et al, *Cancer Immunol. Immunother.,* 40:165–172 (1995) (Fossum II)]. Furthermore, the resulting CTL induced against mutated p21 ras lysed only interferon (IFN)-γ-treated (but not untreated) allogeneic CRC cells, and did not lyse autologous tumor cells.

In the second study, induction of CTL against CRC required specific in vivo and in vitro stimulation of the lymphocytes with carcinoembryonic antigen [K. Tsang et al, *J. Natl. Cancer Inst.,* 87:982–990 (1995)]. The lytic activity of the resulting CTL directed against carcinoembryonic antigen was low, requiring prolonged in vitro stimulation of the CTL and long-term (12–18 hours) incubation to demonstrate lysis by a $^{51}$Cr-release assay.

Both proliferative and cytolytic functions of T lymphocytes directed against tumor cells of various tissue origins have been previously shown to decrease with progression of the disease. Primary, but not metastatic, tumors stimulate patients' autologous T cells in culture [D. Guerry et al, *J. Clin. Invest.,* 73:267–271 (1984) (Guerry I) and D. Guerry et al, *J. Immunol.,* 139:305–312 (1987) (Guerry II)]. T cells from animals and patients with less advanced tumors can lyse autologous tumor cells in vitro [J. Travis, *Science* 258:1732–1733 (1992) and C. Loeffler et al, *J. Immunol.,* 149:949–956 (1992)).

Defective lymphokine production and decreased expression of the ζ chain by lymphocytes infiltrating metastatic tumors have been suggested to underlie the in vivo failure of these lymphocytes to control tumor development [H. Mizoguchi et al, *Science,* 258:1795–1798 (1992); J. Finke et al, *Cancer Res.,* 53:5613–5616 (1993); H. Nakagomi et al, *Cancer Res.,* 53:5610–5612 (1993); and S. Salvadori et al, *J. Immunol.,* 153:5176–5182 (1994)]. T cells derived from peripheral blood mononuclear cells (PBMC) showed higher expression of ζ chain as compared to the tumor-infiltrating T lymphocytes derived from the same patient [Finke, J. H., et al., *Cancer Res.,* 53: 5613–5616 (1993) and H. Nakagomi et al, cited above]. Moreover, advanced (metastatic) tumors, including colon carcinomas, often show reduced expression of MHC class I and class II antigens [C. Cordon-Cardo et al, *Cancer Res.,* 51:6372–6380 (1991); A. Csiba et al, *Br. J. Cancer,* 50:699–709 (1984); and F. Momburg et al, *Int. J. Cancer,* 37:179–184 (1986)].

There exists a need in the art for reagents and methods useful for successful immunotherapy regimens for the treatment of colorectal cancers.

SUMMARY OF THE INVENTION

In one aspect, the invention provides a stable cytolytic T lymphocyte (CTL) cell line established from the peripheral blood mononuclear cells (PBMC) of a patient with minimal residual colorectal carcinoma (CRC) following removal of the primary lesion. The CTL cell line not only lyses the autologous primary CRC, but also lyses allogeneic, HLA-matched metastatic CRC. One such cell line is referred to as CTL007. A therapeutic reagent containing such a cell line in a suitable pharmaceutical carrier is also provided.

In another aspect, the invention provides a method for generating a stable colorectal carcinoma CTL clone by stimulating the lymphocytes of a patient with minimal or no clinical evidence of colorectal carcinoma following removal of the primary lesion in culture with irradiated autologous primary CRC tumor cells and interleukin-2 in the presence of feeder cells, which may be autologous peripheral blood lymphocytes (PBLs) or a lymphoblastoid cell line (LCL), such as Epstein Barr virus transformed B (EBV-D) cells.

In another aspect, the invention provides a therapeutic or diagnostic product derived or produced from, or utilizing, a CTL cell line of this invention. For example, in one embodiment, the invention provides a CRC-associated CTL antigen or peptide fragment identified by the CTL cell line described above, and an immunotherapeutic composition useful in the treatment of CRC containing the antigen or peptide fragment. In another embodiment, the invention provides a factor which is produced by, or secreted by, the cell line. Still other products may be derived from use of the cell lines of this invention.

In another aspect, the invention provides for the identification of a tumor-associated antigen or peptide thereof with high potential for inducing CTL responses in a patient by using a CTL cell line of the invention in a conventional assay known to one of skill in the art.

In yet a further aspect, the invention provides a method for treating a patient with CRC comprising administering to said patient an effective amount of a CTL cell described above.

In still another aspect, the invention provides a method for inducing CTL by stimulating a CRC patient's lymphocytes with autologous CRC tumor cells and IL-2.

In still another aspect, the invention provides a method for bone marrow purging and adoptive transfer therapy of CRC in a patient, by treating bone marrow cells of the patient with a suitable amount of a CTL cell as described herein and reinjecting the treated bone marrow cells into the immunosuppressed patient.

Other aspects and advantages of the present invention are described further in the following detailed description of the preferred embodiments thereof

BRIEF DESCRIPTION OF THE DRAWINGS

FIG. 7A is a bar graph illustrating the cytolytic responses of CD8+ sorted MLT008 cultures (day 50 of MLTC, i.e. day 14 after sort). Lysis of autologous tumor cells WC008 (●), autologous LCLs (■) and natural killer (NK) target cells K562 (▲) by the CD8$^+$ and CD8$^-$ sorted T cells that had received IL-2 from day 8 of culture on was measured in a 6 hour $^{51}$Cr-release assay. "*" indicates that mean CPMs (triplicate determinations) were significantly (p<0.05) higher than the mean CPM of control values (spontaneous $^{51}$Cr-release of target cells).

FIG. 7B is a graph illustrating the cytolytic responses of CD8+ sorted MLT008 cultures that had received IL-2 from day 14 of culture on, and were otherwise treated as in FIG. 7A. Symbols are the same as in FIG. 7A.

FIG. 7C is a graph illustrating the cytolytic responses of CD8– sorted MLTC008 cultures that had received IL-2 from day 8 of culture on, and were otherwise treated as in FIG. 7A. Symbols are the same as in FIG. 7A.

FIG. 7D is a graph illustrating the cytolytic responses of CD8-sorted MLTC008 cultures that had received IL-2 from day 14 of culture on, and were otherwise treated as in FIG. 7A. Symbols are the same as in FIG. 7A.

DETAILED DESCRIPTION OF THE INVENTION

Figure 1:
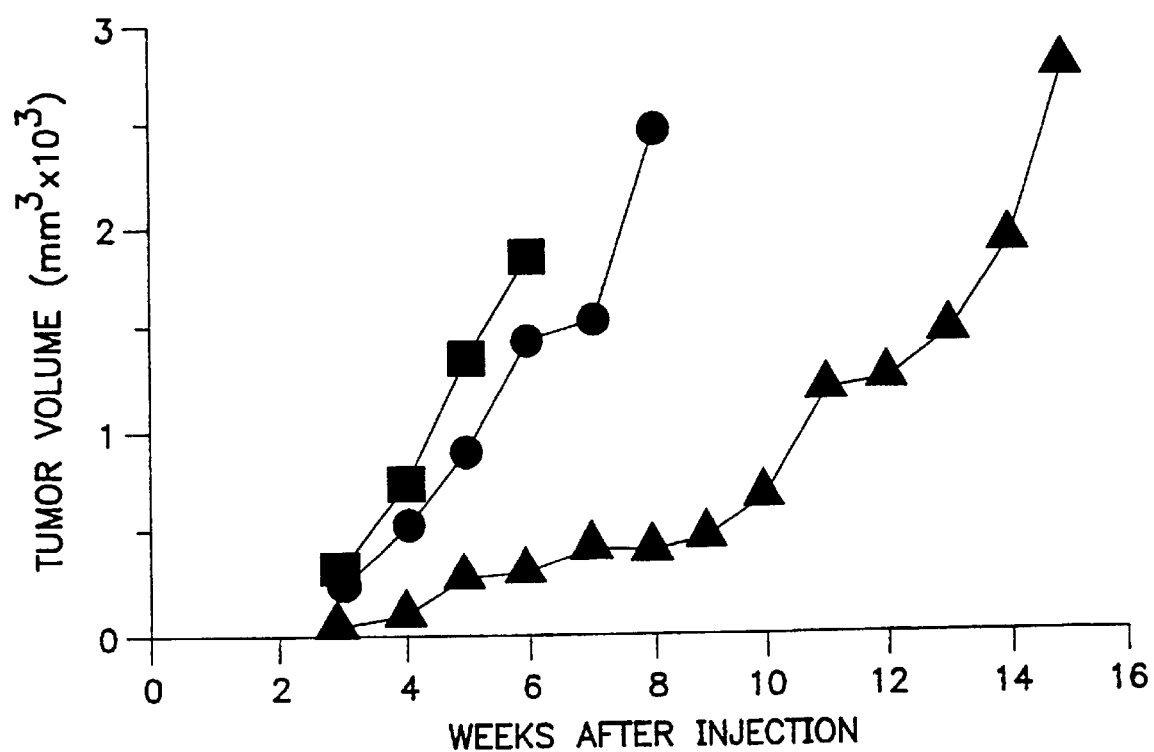
FIG. 1 is a graph depicting the growth of CRC cells WC007 by tumor volume per week after injection in nude mice. Three 6 to 8-week-old nude mice (■, ●, ▲) were injected subcutaneously (s.c.) with $5 \times 10^6$ cells/0.5 ml CRC medium. Tumor sizes were measured once weekly using a Vernier caliper, and volumes were calculated.

According to this invention, methods for generating stable cytolytic T cell colorectal carcinoma cell lines, as well as several exemplary cell lines, are provided. The invention provides methods for employing the cells for diagnosis, therapy and research related to colorectal carcinoma.

A. Methods for Generating CTL Lines and Use Thereof

Without wishing to be bound by theory, the difficulties previously encountered in the induction of CTLs in the PBMC of CRC patients may reflect the inclusion primarily of patients with advanced disease. The CTL of advanced patients may be functionally defective as described above. The present inventors determined that CTLs may be successfully induced in CRC patients with minimal or no clinical evidence of disease following surgical excision of the primary lesion and associated lymph nodes. The inventors discovered that CTL may be successfully induced in the PBMC of such patients. Success in generating CTL against CRC rests, at least in part, in the use of lymphocytes derived from a patient with a primary, rather than metastatic, lesion.

The present invention thus provides a method for producing a stable CTL cell line by stimulating lymphocytes from a CRC patient with primary, non-metastatic disease, including patients with various HLA types, with autologous tumor cells in the presence of Interleukin-2. As described in detail below, a patient with minimal residual, rather than advanced, disease was used as the source of the lymphocytes and tumor cells. The CTLs against CRC induced by the method of this invention may be used to identify antigen/peptides to provide vaccines for HLA-matched CRC patients.

Specifically, in the method of the present invention, mixed lymphocyte tumor cultures (MLTC) were treated with IL-2. Late addition of IL-2 to the cultures may favor the outgrowth of CD4+ lymphocytes, whereas early (day 1–3) addition of IL-2 usually favors the outgrowth of CD8+ CTLs [Kawakami, Y., et al. *J. Exp. Med.*, 168: 2183–2191 (1988); P. van der Bruggen et al, *Science*, 254:1643–1647 (1991)]. As described in detail in Example 3, both the day 8 and the day 14 IL-2 cultures, which consisted of predominantly CD4+ lymphocytes, were sorted into predominantly CD8 and CD8⁻ lymphocytes at an early stage of MLTC (day 36) to increase the probability of obtaining CD8+ CTLs. Only the CD8+-sorted T-cell line which had received IL-2 from day 14 on lysed the autologous tumor cells.

Lysis of the autologous tumor cells by the CTLs is most probably HLA class I-dependent, because WC008 cells express HLA class I, but not class II, and lysis of WC007 by the CTLs is blocked by anti-HLA class I antibody. Other investigators [Fleischer, B., et al., *J. Immunol.*, 136, 1625–1628 (1986) Hayashi et al, cited above; Itoh, K., et al., *Int. J. Cancer,* 52: 52–59 (1992); Kharkevitch et al., 1994; LeMay et al, 1993; Morisaki et al, 1994; Strassman, G., et al., *J. Immunol.*, 133:1705–1709 (1984); Wang, P., et al., *Int. J. Cancer,* 51:962–967 (1992)] have also described CD4+ HLA class I-dependent CTLs. However, in several of those studies [Hayashi et al, cited above; Kharkevitch et al., (1994); LeMay et al., (1993); Morisaki et al, (1994)], target cell lysis by the CD4+ CTLs was weak (requiring overnight incubation of CTL with targets), whereas the CD4+ CTLs described here rapidly (4–6 hours) and effectively lysed (up to 80% lysis) autologous tumor cells. Thus, the lytic capacity of these CD4+ CTLs in vitro is similar to that of CD8+ CTLs and, therefore, CD4+ CTLs may also display similar efficacy in vivo [see, Kawakami II, cited above].

B. The CTL Cell Lines

To inventors' knowledge, they are the first to achieve successful cytolytic T lymphocyte (CTL) induction by stimulation of patients' lymphocytes with autologous colorectal carcinoma tumor cells. Such CTLs are useful to define new colorectal carcinoma (CRC) antigens with high potential for inducing CTL responses in patients. As described in detail in Example 2 below, in an effort to establish CTLs against CRC, peripheral blood mononuclear cells (PBMC) from a patient with minimal residual rectal carcinoma following removal of the primary lesion and involved regional lymph nodes were employed as a source to generate CTLs in culture. The patient (007) had primary CRC, Dukes' stage B2, and currently has no clinical evidence of disease 6 years after resection of the primary tumor.

Successful establishment of a cell line by stimulating the patient's PBMC with cultured autologous tumor cells in Interleukin-2 provided the basis for the generation of the autologous cytolytic T-cell lines. Stable (>3 months) CTL lines and clones from patients 007 and 008, as well as an additional CRC patient (data not shown on third patient) with minimal or no residual disease after surgery have been established. Thus, the inventors established CTL from all three non-advanced patients presently part of these experiments.

One exemplary cloned CTL cell line according to this invention is CTL008 (CD4+). The PBMCs of a patient (008), whose primary rectal carcinoma and regional lymph node metastases (stage Dukes' C) had been removed, were stimulated with autologous tumor cells to generate CTLs. A CD4+, presumably human lymphocyte antigen (HLA) class I (most likely A1 or A3)-dependent, CTL clone was derived that lysed the autologous CRC cells. Allogeneic CRC cells expressing the HLA of the autologous WC008 cells (A1, A3, B57[17],B62[15]) were not lysed by the CTLs. However, it is possible that the allogeneic targets differ from the autologous target in HLA A1 and/or A3 subtype expression (A0101 or A0102; A0301 or A0302). The CTL clone did not lyse autologous Epstein-Barr virus-transformed B (EBV-B) cells, K562 natural killer (NK) cell targets, Daudi lymphokine-activated killer (LAK) cell targets, or allogeneic HLA non-matched CRC cells. The CTL clone did not lyse an autologous lymphoblastoid cell line (LCL). The specificity of the uncloned and cloned CTL008 is restricted to autologous colorectal carcinoma cells, since allogeneic, HLA-nonmatched or partially matched allogeneic CRC cells were not lysed.

CD4 is involved in target cell recognition by the CTL. This CTL clone expresses two T-cell receptor variable a chains (V$\alpha$22 and V$\alpha$11) and one $\beta$ chain (V$\beta$14).

In contrast to prior art descriptions of this type of CTL, the CTLs of this invention rapidly lyse autologous CRC cells. This CTL line is IL-2-dependent and produces IFN-$\gamma$, a cytokine secretion pattern characteristic of Th1-type cells [T. Mosman et al, *J. Immunol.*, 136:2348–2357 (1986) and P. Parronchi et al, *Proc. Natl. Acad. Sci. USA*, 88:4538–4542 (1991)].

The cloned cell line offers the advantage over other cell cultures of being immortal, i.e., permanently and rapidly growing in vitro in the presence of recombinant human (rh)IL-2, and thus provides unlimited material for in vitro and in vivo research, diagnostic and therapeutic uses. Another advantage of these cells is that they are phenotypically and functionally stable.

Another exemplary CTL line is CTL007, which consists predominantly of CD4+ lymphocytes, and is homogeneous with respect to CD3 and CD4 markers (93 and 96% of the cells positive, respectively), but heterogeneous with respect to V$\beta$ TCR expression, after approximately 4 months in culture. Since lysis of target cells seems to be dependent on both HLA-A1 and -A3 expression, more than one antigen may be recognized by the uncloned CTL. The cytokine secretion pattern of the CTL line was of the Th1- and Th2-type.

The CTL line CTL007 lysed the autologous colorectal carcinoma cells, and the allogeneic, HLA A1 or A3-matched CRC cells, but not the autologous EBV-B cells, K562 (natural killer target) cells or Daudi LAK cells. Lysis of autologous tumor cells most likely was HLA class I-restricted. These CTL not only lyse the autologous primary CRC, but also allogeneic, HLA-matched metastatic CRC. This immortalized cell line CTL007 has been deposited with the American Type Culture Collection, 10801 University Boulevard, Manassas, Va. 20110-2209 on Apr. 22, 1998 and assigned accession number CRL12518 under the conditions specified by the Budapest Treaty for the International Deposit of Microorganisms for Patent Purposes.

Thus, CTLs were established from three nonadvanced patients included in this study. In contrast, other investigators have failed to establish CTLs from the lymphocytes of CRC patients with advanced disease, as described in the background. The CTL clones prepared according to this invention are useful in a variety of diagnostic and research assays, as discussed below.

C. The CTL Antigen

The CTL antigen defined by CTL007 is present on allogeneic CRC cell lines. Based on the descriptions of the cell lines above, the CRC antigen recognized by the CTL008 cells may be individually specific for the autologous tumor. Alternatively, allogeneic tumor cells may express the tumor-associated antigen but may lack appropriate HLA subtype expression.

The antigen(s) recognized by the CTL lines of the present invention may be identified using conventional molecular approaches (i.e., cloning of the antigen using COS cell libraries) such as those described by P. van der Bruggen et al, *Science*, 254:1643–1647 (1991). Alternatively, the peptide may be isolated using high pressure liquid chromatography (HPLC) and mass spectrography by techniques, such as described by Cox et al, *Science*, 264,716–719 (1994).

The CTL-defined antigen, or a peptide fragment thereof identified by use of the above described clones or cell lines, may be used as a vaccine component or immunotherapeutic composition in active immunotherapy for HLA-matched CRC patients (having primary or metastatic CRC), similar to the uses described for the melanoma CTL-defined antigens [see, e.g., Kawakami II and III, cited above, and Cox, A. L, et al. *Science*, 264,716–719 (1994)].

D. Utility of the Invention

The CTL clones of the present invention may be used not only to identify useful CRC antigens useful in the preparation of vaccines, but also the cell lines may be useful directly in immunotherapies of CRC using adoptive CTL immunotherapy in processes similar to that applied to adoptive immunotherapy of melanoma [Kawakami II, cited above and incorporated by reference].

1. Therapeutic Uses

The CTL-CRC cell lines (CTL007 and CTL008) of the invention, particularly the stable cell line CTL007, are suitable for use in adoptive immunotherapy of colorectal cancer in HLA-matched recipients, as well as for eradication of residual malignant cells from patient's bone marrow (marrow purging). For immunotherapy, the cell lines may be used in treatment of any HLA-matched patient. For example, a suitable number of the stable CTL cells are administered to an HLA-matched recipient host. Preferably, the mode of administration involves injecting the cells i.v. in saline. Multiple injections of the CTL cells are administered as deemed to be necessary by one of skill in the art.

Alternatively, the cells of this invention may be used in a method for bone marrow purging and adoptive transfer therapy of CRC in a patient. This method involves removing bone marrow cells from a patient; treating the bone marrow cells ex vivo with a suitable amount of a cell line of the invention, and reinjecting the treated bone marrow cells into the patient. Again selection of the amount of cells to be used per amount of marrow, and the regimen of readministration are within the knowledge of the art.

For any such therapeutic use, the appropriate dosages and therapeutic regimen follow those known and previously described for melanoma CTL adoptive immunotherapy. One of skill in the art and preferably an attending physician, can readily alter dosages or therapeutic regimens to suit the particular individual patient based on factors such as general health, age, weight, disease state, etc.

2. Antigen Isolation/Production of Other Factors

In culture, a variety of growth factors, cytokines, and/or other proteinaceous molecules may be produced from or derived from these CTL lines. Such products produced or derived from the use of the CTL lines of this invention may be used in therapeutic or diagnostic regimens, and as such, form part of this invention. For example, certain products may be secreted from the growth of the CTL cells in culture, e.g., growth factors, cytokines, etc.

Further, the CTL lines of this invention may be used to identify CRC antigens, and permit the isolation of such antigens, such as by contacting biological material from a CRC patient with a CTL or CTL clone of the invention and isolating the biological material, i.e., protein or antigen, which binds to, and in turn, stimulates the growth of the CTL. The antigen may be identified by CTL stimulation/proliferation assays as described herein. Suitable isolation techniques are described above, and available to one of skill in the art. The resulting CRC antigen and peptide fragments thereof are useful in therapeutic compositions and diagnostic assays.

The antigen itself may be useful as a vaccine component. Alternatively, the antigen or a peptide thereof may be used to produce antibodies (polyclonal, monoclonal, recombinant, synthetic, chimeric or humanized), which may themselves be employed in therapeutic compositions or as passive vaccine components. Such antibodies may also be employed in diagnostic regimens to diagnose CRC by detecting the CRC antigen.

3. Diagnostic Uses/Drug Screening

The CTL cells themselves may be employed in diagnostic protocols. For example, the CTLs may be contacted with patient serum and the ability of the serum to stimulate CTL observed according to conventional assays described herein. Stimulation with a patient serum may be indicative of some stage of CRC. Thus, the cells may form an assay to detect CRC or its recurrence.

The cells may also be employed in similar assays for the evaluation or screening of test compounds which stimulate CTLs. Using a proliferation assay, such as the ones described in the following examples, a test compound is exposed to the CTL cells in culture and the culture is observed for stimulation. Test compounds may thus be screened for stimulating or not stimulating the CTLs. Such compounds may be employed either in other assays or in therapeutic compositions for the treatment of cancers or in protocols for the development of other drugs useful in the diagnosis or treatment of cancer.

The following examples illustrate various aspects of this invention and do not limit the invention, the scope of which is embodied in the appended claims.

EXAMPLE 1

Antibodies and Cell Lines of the Prior Art

The following table lists the antibodies and cell lines used in these examples and provides the commercial or institutional sources of same or published references describing same. All CRC cell lines were grown in CRC medium. All lymphoid cell lines were maintained in RPMI 1640 (JRH Biosciences, Lenexa, Kans.) supplemented with 10% fetal bovine serum (FBS).

TABLE 1

| Mabs/Cell Lines | Source |
| --- | --- |
| Murine anti-CRC MAb GA733 | M. Herlyn et al, Proc. Natl. Acad. Sci. USA, 76:1438–1442 (1979) (Herlyn I); D. Herlyn et al, J. Immunol. Meth., 73:157–167 (1984) (Herlyn II) |
| Murine anti-CRC MAb CO17-1A | Same as above |
| HLA-A, -B, -C-specific murine MAb W6/32 (IgG2a) | B. Perussia, Thomas Jefferson University (Philadelphia, PA) |
| Pan HLA-A specific murine MAb 131 (IgG1;25) | J. Kornbluth, University of Arkansas (Little Rock, AR). |

TABLE 1-continued

| Mabs/Cell Lines | Source |
| --- | --- |
| Pan HLA-B-specific MAb 4E (IgG2a) | Yang, S. Y., et al., Immunogenetics 19:217–231 (1984); S. Y. Yang, Memorial Sloan Kettering Cancer Center New York, NY). |
| HLA-B12- and HLA-B48/60-specific human IgM MAbs 13E12.2F11 and 2C10.B12 | A. Mulder et al, Hum. Immunol., 36:186–192 (1993); gift of A. Mulder, Leiden University Hospital (Leiden, The Netherlands) |
| Murine MAbs reactive with HLA-A1/36, HLA-A3, HLA-B35/55/75/44, HLA-B62[15]-B57[17], -DR7 and -DR4 (all of IgM isotype) | One Lambda Corporation (Canoga Park, CA) |
| Murine MAb H24B5 (IgG2a) anti-influenza virus hemagglutinin) | Gift of W. Gerhard, The Wistar Institute |
| Murine Mab B66.6 (IgG1, anti-CD4) | Gift of G. Trinchieri, The Wistar Institute |
| MAb OKT3 (IgG1, anti-CD3) | American Type Culture Collection (ATCC, Rockville, MD) |
| MAb GAP A3 (IgG$_{2a}$; anti-HLA-A3) | ATCC |
| MAb OKT8 (IgG2, anti-CD8) | ATCC |
| Murine MAbs specific for CD3, CD4, CD8, CD-20, HLA-DP, -DQ (all IgG1) and -DR (IgG2a) | Becton Dickinson (San Jose, CA) - for FACS analysis. |
| Anti-DR MAb D1.B.6 (IgG1) | ATCC |
| MAb 3G8 specific for CD16 (IgG1) | H. Fleit et al, Proc. Natl. Acad. Sci. USA, 79:3275–3279 (1982); J. C. Unkeless, Mount Sinai Medical Center (New York, NY) |
| Murine MAbs specific for human TCR α/β constant and variable regions [βV5(a), βV6(a) and βV12(a)] | T Cell Sciences (Cambridge, MA) |
| MAbs B133.1.1 and B133.5.1 to IFN-γ (IgG1) | T. van der Pouw Kraan et al, Eur. Cytokine Netw., 4:343–349 (1993); G. Trinchieri, The Wistar Institute |
| MAbs B154.9.2 and B154.7.1 to TNF-α (IgG1) | Same as above |
| MAbs 4F2, 5AG, and 5A4 to IL-4 (IgG1) | Same as above |
| CRC cell lines HT-29, LS180, WiDR, LoVo, SW48, SW480 and SW837 | ATCC |
| LAK target cell line Daudi (human Burkitt lymphoblastoid cell line) | ATCC |
| NK target cell line K562 (Human erythroleukemia cell line) | ATCC |

EXAMPLE 2

CRC Cell Lines of the Invention

A. CRC Cell Line WC007

CRC cell line WC007 (HLA-A1, -A3, -B35, DR) was established in vitro from a rectosigmoid lesion of a moderately differentiated adenocarcinoma derived from a 76-year-old female (patient 007). Patient 007's HLA type was A1, A3, B35, B40, Cw4, Cw8 DR], DR4, DQ5, DQ8, DP2, DP4. The lesion extended through the entire thickness of the bowel wall and into the pericolic adipose tissue. None of the nine regional lymph nodes examined was positive for metastatic carcinoma; the lesion was thus classified as Dukes' stage B2. At present (6 years after resection of the tumor), the patient shows no evidence of disease.

To establish the WC007 cell line, the specimen was finely minced using sterile scalpel blades, washed in Hanks Balanced Salt Solution (HBSS), digested with 150 U/ml of hyaluronidase (Sigma, St. Louis, Mo.) for 2–3 hours at room temperature, and rewashed in HBSS. Cells were plated in 24-well plates (Corning, Corning, N.Y.) in CRC medium, which contains MCDB 201 medium containing 20% L15 medium, 5 mM L-glutamine, 0.05% NaHCO$_3$, 100 U/ml penicillin, 50 µg/ml streptomycin, 0.25 µg/ml FUNGIZONE anti-fungal, 5 µg/ml insulin and 2% heat-inactivated FBS. All reagents were obtained from Sigma. Wells were pre-coated with VITROGEN type I collagen (Collaborative Research, Waltham, Mass.) before cells were plated.

Cells grew exponentially after about 1 year in culture and the established CRC WC007 line is currently at passage 50. Characteristics of the CRC cell line WC007 are identified in Table 2 below. HLA alleles in bold in Table 2 are predominantly reactive with MAbs. The % cells binding reports the binding of MAbs GA733, CO17-1A, and anti-HLA-A, -B, -DP, and -DQ to WC007 CRC cells, measured in indirect immunofluorescence test, using fluorescein-isothiocyanate (FITC)-labeled goat anti-mouse IgG [F(ab')$_2$-specific] as secondary antibody. Binding of murine or human IgM MAb was measured in indirect immunofluorescence test using FITC-labeled donkey anti-mouse IgM or FITC-labeled goat anti-human IgM as secondary antibodies. Binding of FITC-labeled W6/32 (anti-HLA-A, -B, -C) or L243 (anti-HLA-DR) was measured in direct immunofluorescence test using FITC-labeled MAb to these HLA. Autologous EBV-B cells served as positive control cells for all anti-lLA MAb. All values (means±SD of 2–5 independent experiments) are corrected for binding of irrelevant, isotype-matched control MAb. HLA Cw4 and Cw8 were absent in complement-dependent cytotoxicity assay.

TABLE 2

Characteristics of CRC Cell Line WC007

| MAb Name | MAb Species of origin | MAb Isotype | MAb Specificity | % Cells binding MAb (±S.D.) |
|---|---|---|---|---|
| GA733 | Mouse | IgG2a | CRC | 91.5 ± 12.6 |
| CO17-1A | Mouse | IgG2a | CRC | 76.8 ± 32.1 |
| W6/32 | Mouse | IgG2a | HLA-A, -B, -C | 64.7 ± 25.4 |
| 131 | Mouse | IgG1 | HLA-A | 86.7 ± 6.7 |
| 4E | Mouse | IgG | HLA-B | 69.5 ± 5.6 |
| 289 HA-1 | Mouse | IgM | HLA-A1, -36 | 13.8 ± 9.2 |
| 378 HA-1 | Mouse | IgM | HLA-A3 | 19.4[a] |
| 601 HA-1 | Mouse | IgM | HLA-B35, -55, -75, -44 | 18.6 ± 16.3 |
| 2C10.B12 | Human | IgM | HLA-B48, -60 | 0 |
| L243 | Mouse | IgG1 | HLA-DR | 42.0[a] |
| B7/21 | Mouse | IgG1 | HLA-DP | 0 |
| SK10 | Mouse | IgG1 | HLA-DQ | 0 |

[a]Values are derived from IFN-γ-treated cells (500 U/ml for 48 hours for HLA-A3, and 200 U/ml for 72 hours for HLA-DR); non-treated cells were negative.

EBV-transformed B-cell lines of patient 007 were established from freshly isolated PBMC using 2.5 transforming units per cell of B95-8 virus (Tampa Bay Research Institute, Tampa Bay, Fla.).

B. CRC Cell Line WC008

CRC cell line WC008 was established from a tumor sample of female patient 008, who was 48 years old at time of surgery. The HLA type of patient 008 was determined as A1, A3, B57[17], B62[15], Cw3, Cw6, DR4, DR7, DQ8[3], DQ9[3], DPB1*0301, DPB1*1301. Six small lesions (the largest of which measured 13×7×6 mm) were excised from the distal part of the rectum. The lesions were identified as intermediate grade adenocarcinoma invading the muscularis mucosae, with metastases to 15 perirectal lymph nodes (stage Dukes' C). The patient received a combination of chemo- and radiation therapy for a continuous period of 2 years, starting 1 month after surgery, and succumbed to the disease 4 months after therapy was ended.

The fresh tumor specimen was minced, and washed two times in CRC medium, which contained MCDB 201-medium containing 20% L15 medium, 10 mM L-glutamine, 0.05% NaHCO$_3$, 10 U/ml penicillin, 50 µg/ml streptomycin, 1.25 µg/ml FUNGIZONE anti-fungal (Bio Whittaker, Walkerville, Md.), 5 µg/ml insulin and 2% heat-inactivated fetal bovine serum (FBS). Unless otherwise indicated, the reagents were obtained from Sigma, St. Louis, Mo. The minced specimen was resuspended in ice-cold CRC medium containing 20% MATRIGEL matrix (Collaborative Biomedical Products, Bedford, Mass.) to give a suspension containing 20–40% tumor tissue.

The tumor sample was passaged in severe combined immunodeficiency (SCID) mice before adaptation to growth in vitro. The CB17 SCID mice were initially obtained from M. Bosma (Fox Chase Cancer Center, Phila. Pa.) and are currently bred at the Wistar Institute Animal Facility. Mice were routinely tested for circulating murine IgM levels at age 6 weeks, and only animals with 1 µg/ml of IgM were used. All animals were housed under pathogen-free conditions in microisolator cages and were handled under a laminar flow hood. One milliliter of the minced tumor suspension was injected s.c. into each of 3 SCID mice.

Palpable tumors were observed 1 month after injection in all 3 mice. After an additional month, all mice had large tumors, which were excised and passaged in additional SCID mice or adapted to in vitro growth by plating the tumor cells in T75 tissue culture flasks (Falcon, Franklin Lakes, N.J.) precoated with 20% MATRIGEL matrix in L-15 medium.

The lymphoblastoid cell line (LCL) was established from the fresh PBMC of patient 008 using 2.5 transforming U/cell of B95-8 virus (Tampa Bay Research Institute, Tampa Bay, Fla.). All LCLs were maintained in RPMI 1640 medium (JRH Biosciences, Lenexa, Kans.) supplemented with 10% FBS.

C. Additional CRC Cell Lines

CRC cell lines WC013, WC010 and WC016 from CRC patient of Dukes' stage B, C and B, respectively, were also established substantially as described above for WC008, but without prior SCID passage.

EXAMPLE 3

Establishment of T-Cell Lines

PBMC of the selected patient, e.g., 007 or 008, were isolated by Ficoll Hypaque (Pharmacia, Uppsala, Sweden) centrifugation of heparinized blood and cryopreserved. Defrosted PBMC were plated in 96-well round-bottom plates (Corning, Corning, N.Y.; 1×10$^5$ cells/well) together with irradiated (10,000 rads, $^{137}$Cs source) patient CRC cells, e.g., WC007 or WC008 (5×10$^4$ cells/well) in T-cell medium. For the CTL007 cell line, the medium was RPMI 1640 containing 10% FBS. For the CTL008 cell line, the medium was RPMI 1640 containing 10% pooled human AB serum, 10 mM HEPES and 0.05 mM 2-mercaptoethanol (all from Sigma).

A. CTL007 Cells

For CTL007 cells, seven days later, cells were transferred to 96-well flat-bottom plates (Corning) and restimulated with irradiated autologous tumor cells (2×10$^4$ cells/well) under the same conditions. Lymphocyte proliferation was obvious from day 12 of culture. On day 15, all proliferating lymphocytes in both the presence or absence of IL-2 were restimulated with autologous tumor cells (5×10$^4$ cells/well) and IL-2. On day 23, cells of 12 wells of each culture were pooled into one well of a 24-well plate (Corning) and restimulated with irradiated autologous tumor cells (1×10$^5$ cells/well) and IL-2 (20 U/ml) in the presence of autologous irradiated (3,000 rads) PBMC as feeders. T cells were then restimulated weekly with tumor cells and IL-2. EBV-B cells from an allogeneic healthy donor were used as feeders once in week 7 of MLTC.

From week 8 on, T cells were restimulated weekly with tumor cells, IL-2 and autologous PBMC or EBV-B as feeder cells. T cell growth rates of both cultures (IL-2 on day 7 or 15) were stable for >4 months, decreasing thereafter. CTL007 showed doubling times of 2–3 days during the initial 6 weeks of culture. Growth rates of the cells were stable for >4 months. Attempts to clone the CTL in the presence of WC007 CRC cells, IL-2 and autologous EBV-B cells were unsuccessful.

B. CTL008

For CTL008, lymphocyte proliferation was detectable on day 6 of culture. On day 8 of MLTC, cells were transferred to 24-well flat-bottom plates (Corning; 2×10$^6$ cells/well) and restimulated with irradiated autologous WC008 tumor cells (2×10$^5$ cells/well) in the presence or absence of 20 U/ml natural IL-2 (Boehringer Mannheim, Germany). On days 14 and 31 all proliferating lymphocytes in both the presence or absence of IL-2 were restimulated with autologous tumor cells (5×10$^4$ cells/well) and IL-2.

On day 36, both MLTC cultures (receiving IL-2 from days 8 or 14 on) were sorted by fluorescence-activated cell sorting (FACS) into predominantly CD8+ and CD8$^-$ populations by staining the cells with anti-CD8 MAb followed by FITC-labeled goat anti-mouse IgG-F(ab')$_2$. CD8+ and CD8$^-$ cells were cultured with IL-2-containing T-cell medium in 24-well plates coated with 30 µg/ml of MAb OKT3. From day 41 on, T cells were restimulated weekly with IL-2, irradiated autologous CRC cells (at a responder-to-stimulator ratio of 10:1) and irradiated (10,000 rads) and autologous EBV-B cells as feeder (at responder-to-feeder ratios of 0.5:1 to 1:1). In some experiments autologous EVB-B cells were substituted with allogeneic or autologous PBMCs.

The CD8$^+$-sorted CTL line initiated with IL-2 on day 14 was cloned on day 86 (when the majority of the cells were CD4$^+$; Table 3) by stimulating the T cells with anti-CD3 MAb OKT3. T cells were serially diluted in 96-well round-bottom microtiter plates containing 0.5×10$^4$ irradiated WC008 cells, 1×10$^5$ irradiated autologous EBV-B cells and 4 U of IL-2 per well in 200 µl of T-cell medium. Wells had been precoated with 30 µg/ml of anti-CD3 MAb OKT3 in PBS (Ca++- and Mg++-free) for 2 hours at room temperature, and then washed once in PBS (Ca++- and Mg++-free). After 7 days, T cells were restimulated with 1×10$^4$ irradiated WC008 cells, 2×10$^5$ autologous EBV-B cells and 4 U of IL-2 per well, and transferred to 96-well flat-bottom plates (Corning) precoated with MAb OKT3. On days 14 and 21, CTLs were restimulated with IL-2, 7.5×10$^4$ irradiated allogeneic PBMC, 2.5×10$^4$ irradiated autologous EBV cells and 4×10$^3$ WC008 cells/well. From day 26 on, proliferating T cells were restimulated in 96-well round-bottom plates or 48-well plates (Costar, Cambridge, Mass.) as described above for the T-cell line.

Twenty-six days after cloning, 5–98% of the wells seeded with various numbers of T cells showed cell growth and lymphoproliferative responses. Only one clone (CTL008cl.C2) showed stable (approximately 3 months), but slow growth.

EXAMPLE 4

HLA-Typing

HLA-A, -B, and -C typing was performed serologically on patient's autologous T cells activated nonspecifically with anti-CD3 MAb OKT3 (ATCC), fresh patient PBMC, EBV-B or the newly established CRC cell lines of Example 2 in complement-dependent microcytotoxicity assay by using tissue microtiter typing trays (One Lambda, Canoga Park, Calif.). For HLA-class II and HLA-Cw typing, group-specific polymerase chain reaction (PCR) primers were used to amplify DR, DP, DQ, Cw3 and Cw6 loci from genomic DNA isolated from the patients' autologous EBV-B cells or from cDNA isolated from the patients' CRC cells. Alleles were then identified by dot blot hybridization with sequence-specific oligonucleotide probes. Genomic typing was confirmed by complement-dependent microcytotoxicity assay (HLA-Cw3, -Cw4, Cw6 and -Cw8) and flow cytometry (HLA-DR, -DP and -DQ; see Example 8).

The results of the assays on the five newly established CRC cell lines (WC-007, -008, -010, -013, -016) are as follows. All of the five cell lines of Example 2 express the 40 kDa gastrointestinal carcinoma-associated glycoprotein defined by MAbs CO17-1A and GA733 and HLA-A and -B molecules. The five different CRC lines have been maintained in culture for 10 to 60 passages.

Expression of HLA-A and -B alleles was examined in CRC cell line WC007 based on the HLA-type of the same patient's PBMC. Table 2 above illustrates the results.

HLA-A1 and -B35 were constitutively expressed by the WC007 CRC cells, whereas HLA-A3 could only be detected after treatment of the cells with IFN-γ. HLA-B48, -Cw4, and -Cw8 could not be detected in WC007 CRC cells. In positive control experiments, the patient's autologous EBV-B cells expressed all 4 alleles tested. HLA-DR, but not -DP or -DQ expression was upregulated in CRC WC007 by IFN-γ treatment.

T cells (15 weeks in culture) were analyzed for direct binding of PE-labeled MAb to CD3, CD4, or CD8, or FITC-labeled MAb to HLA-DR; binding of unlabeled MAb to CD16 or TCR α/β was detected by FJTC-labeled goat anti-mouse IgG [F(ab')$_2$-specific]. The assays were repeated at least once with similar results. All values are corrected for binding of irrelevant, isotype-matched control antibody. The results are reported in Table 3 below.

Greater than 90% of the CTL007 expressed CD3, CD4, HLA-DR, and TCRα/β (Table 3).

TABLE 3

| Surface Marker Expression by CTL007 | |
|---|---|
| Surface Markers | % CTL Cells positive |
| CD3 | 93 |
| CD4 | 96 |
| CD8 | 0 |
| CD16 | 1 |
| HLA-DR | 90 |
| TCR α/β | 94 |

The phenotypic characteristics of the two WC008 MLTC that received IL-2 on day 8 or 14, respectively, were similar, i.e., they expressed TCR α/β, CD3, CD4, CD8, HLA A, B and C and DR (Table 3). FACS sorting of the two WC008 MLTC with anti-CD8 MAb on day 36 resulted in the isolation of predominantly CD8+ and CD8-lymphocytes. The CD8+-sorted T cells grew exponentially with much shorter doubling times than the CD8$^-$-sorted T cells (2–3 vs. 6–7 days), following stimulation with both autologous tumor and EBV-B cells.

The HLA phenotype of the WC008 cells is A1, A3, B57[17],B62[15]. Phenotypic analysis of the CTL008 clone revealed 95% CD3$^+$ and 91% CD4$^+$ cells.

Further phenotypic analyses of T-cell lines derived from one patient are reported in Table 4 below. In Table 4, for percent cells positive for surface marker expression, all values are corrected for binding of irrelevant, isotype-matched control antibody. The IL-2 column represents the day on which IL-2 was first added. In Table 4, the abbreviation "nt" means not tested. The lymphocytes were sorted on day 36 of MLTC.

To determine whether the CD4 marker on the CTL007 and HLA-DR on the target cell are involved in the target recognition by the CTL, proliferation assays using MAbs to these markers were performed. Antigen-specific proliferation of the CTL007 was significantly inhibited by anti-CD4 MAb B66.6 (28% inhibition; p<0.05 as compared to isotype-matched control MAb), but not by anti-HLA-DR MAb D1.B.6.

TABLE 4

PHENOTYPIC ANALYSIS OF T-CELL LINES DERIVED FROM ONE PATIENT

| Lymphocyte Cultures | | | Surface Marker Expression (% Cells +) | | | | | | | |
|---|---|---|---|---|---|---|---|---|---|---|
| FACS | IL-2 | Days in Culture | TCR $\alpha/\beta$ | CD3 | CD4 | CD8 | HLA-DR | HLA-A, -B, -C | CD20 | CD16 |
| Unsorted | 8 | 35 | 73.3 | 82.1 | 66 | 29.8 | 43.4 | 82.9 | 0 | nt |
| Unsorted | 14 | 35 | 59.6 | 47.5 | 39.8 | 17.9 | 39.1 | 81.9 | 0 | nt |
| CD8+ sorted | 8 | 70 | nt | nt | 28.8 | 71.7 | 81.5 | nt | nt | 0 |
| CD8+ sorted | 14 | 70 | nt | nt | 22.5 | 79.6 | 86 | nt | nt | 0.1 |
| CD8– sorted | 14 | 84 | 93.8 | 97.8 | 64.6 | 27.6 | 78.3 | nt | nt | nt |
| CD8– sorted | 14 | 106 | nt | nt | 67.3 | 35.7 | nt | nt | nt | nt |

EXAMPLE 5

Tumorigenicity of CRC Cell Lines of the Invention

A. WC007

Three 6- to 8-week old female nude mice (nu/n BALB/c background, Harlan Sprague Dawley, Indianapolis, Ind.) were injected s.c. with $5\times10^6$ WC007 cells in 0.5 ml of CRC medium. Tumor volumes were measured weekly with a caliper. Animals with tumors >1 cm maximal diameter were euthanized.

B. CRC Cell Lines WC-008, -010, -013 and -016

These cell lines were propagated as described above for the WC007 cells, except in SCID mice.

C. Results

All five CRC cell lines were tumorigenic in SCID or nude mice (shown for WC007 cells in FIG. 1). Histological examination of tumors derived from WC007 cells showed that they were well vascularized, moderately differentiated adenocarcinomas and did not infiltrate into muscle, regional lymph nodes or distant organs.

EXAMPLE 6

Proliferation Assays

A. CTL007

T cells (week 9 of MLTC; $1\times10^4$ non-CTL or $0.5\times10^4$ CTL per well) were plated in 96-well flat-bottom plates with irradiated EBV-B cells (10,000 rads, $5\times10^4$ cells/well), IL-2 (20 U/ml) and various numbers of tumor cells to give stimulator (tumor):responder (T cell) ratios of 0.25:1, 0.5:1, 1:1, and 2:1. In blocking experiments, MLTC were incubated with anti-BLA-DR MAb D1.B.6, anti-CD4 MAb B66.6 (both at saturating concentration of 1 $\mu$g/ml), or isotype-matched control MAb. After 7 days of incubation at 37° C. in a humidified $CO_2$ incubator, cells were pulsed with $^3$H-thymidine (1 $\mu$Ci/well) for at least 6 hours. Cells were then harvested on filter mats using a semi-automated cell harvestor (Skatron Instruments, Inc. Sterling, Va.) and radioactivity was assessed in a $\beta$-liquid scintillation counter. All determinations were performed in triplicate.

Figure 2:
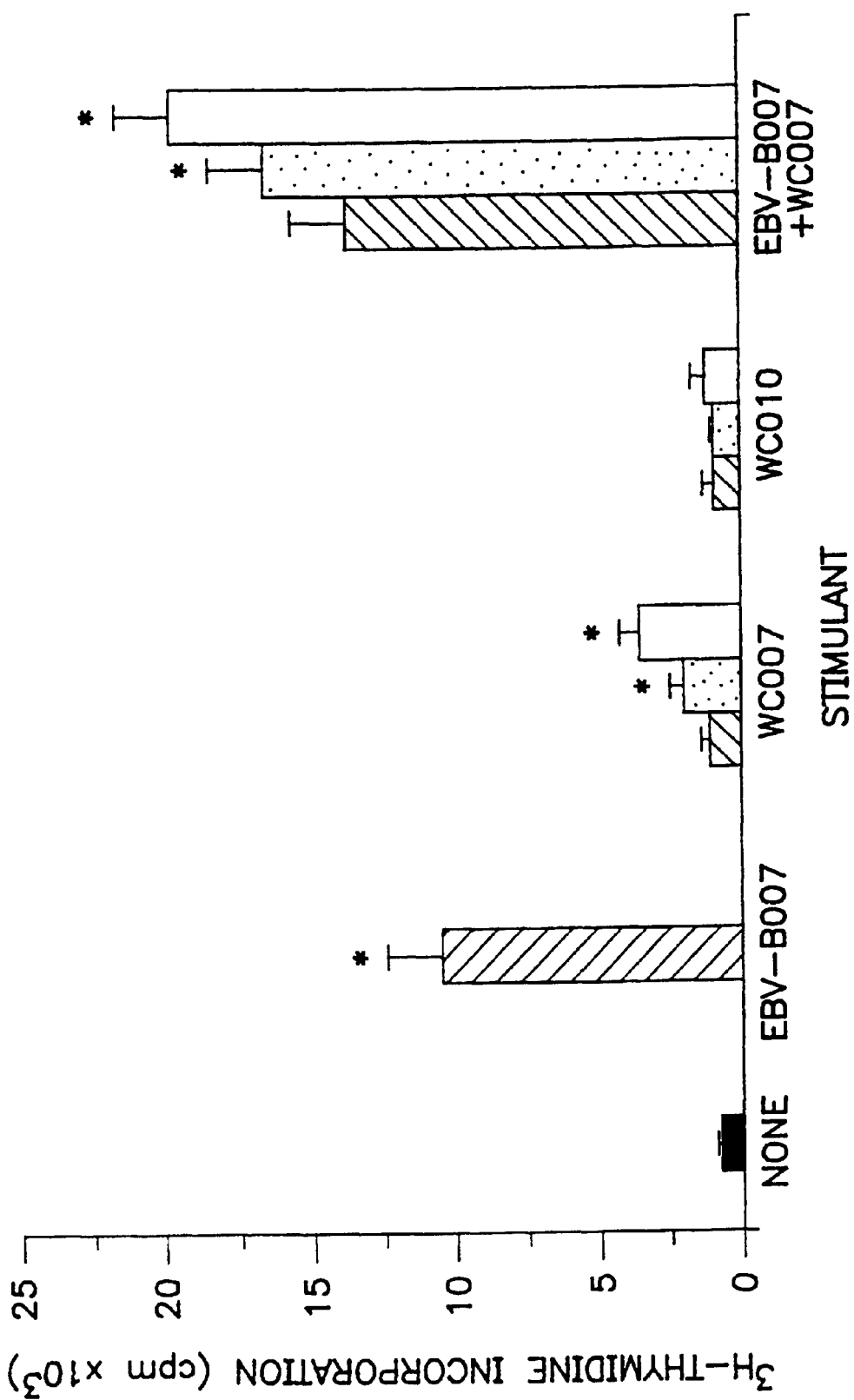
FIG. 2 is a graph depicting the growth dependency of CTL on autologous EBV-B and tumor cells. T cells (7 weeks in culture) were cultured in the presence of IL-2, but the absence of autologous tumor and EBV-B cells for 2 weeks. T cells were then stimulated with irradiated autologous EBV-B cells at EBV-B-to-T cell ratio of 5:1, and/or irradiated autologous WC007 CRC cells at stimulator-to-responder cell ratios of 0.5:1 (horizontal lines), 1:1 (dots), and 2:1 (open bar). The asterisk * indicates values that are significantly ($p<0.05$, Student's t test) different from control values (T cells plus IL-2 only; black bar). All values obtained with EBV-B and tumor cells (except for EBV-B007 plus WC007 cells at ratio 0.5:1) are also significantly ($p<0.05$) different from the values obtained with EBV-B007 only (bar with diagonal lines).

Proliferation of the CTL007 line was dependent on the presence of both autologous tumor and EBV-B cells (FIG. 2).

B. CTL008

T cells (day 44 of culture, i.e. day 8 after sorting; $1\times10^4$ cells/well/0.2 ml) were cultured with irradiated (10,000 rads) autologous WC008 tumor cells ($1\times10^4$ cells/well) in 96-well flat-bottom plates in the presence of IL-2 (20U/ml). After 7 days of incubation at 37° C. in a humidified $CO_2$ incubator, cells were pulsed with [$^3$H]thymidine (1 $\mu$Ci/well) for approximately 6 hours. Cells were then harvested on filter mats using an automated 96-well plate cell harvesting system (Tomtec, Orange, Conn.), and radioactivity of dried filter mats was measured in a MATRIX 96 direct beta counter v1.53 (Packard, Downers Grove, Ill.). All determinations were performed in triplicate.

In the co-cultures of PBMC and irradiated autologous tumor cells of patient 008, lymphocyte proliferation was detectable beginning on day 6 of MLTC. MLTC that had received IL-2 from day 8 on showed doubling times of 2–3 days during the initial 5 weeks of culture, whereas the MLTC that had received IL-2 from day 14 on showed doubling times of 5–7 days. During the first 5 weeks of culture, T cells were stimulated with tumor cells and IL-2 only, in the absence of autologous EBV-B cells or PBMCs as feeders.

The proliferative activities of the CD8+-sorted T cells that received IL-2 from day 14 of culture on were significantly higher (p<0.05) than the activities of CD8+-sorted T cells that received IL-2 from day 8 on or compared with CD8−-sorted T cells (IL-2 on day 8 or 14) (FIGS. 5A–5D). The proliferation of the CD8+-sorted cells (day 14 IL-2) measured 8 days after the sort was highest after stimulation with both autologous tumor and EBV-B cells, as compared to stimulation with either of the 2 cell types alone (FIGS. 5A–5D).

EXAMPLE 7

Cytotoxicity Assay

This assay was performed as previously described [R. Somasundaram et al, *Cancer Immunol. Immunother.*, 27:183–189 (1988)]. Adherent CRC cells were trypsinized the day before the assay and allowed to adhere overnight.

The next day, CRC cells were detached with EDTA. All CRC cell lines, 0.5–2×10$^6$ cells/0.5 ml of RPMI 1640 medium (supplemented with 10% FBS), were labeled with 100–150 μCi of Na$^{51}$CrO$_4$ (DuPont NEN, Boston, Mass.) for 30 minutes at 37° C. Other target cells used in the cytotoxicity assays and growing in suspension were labeled similarly.

Labeled target cells were then washed 3 times and between 2×10$^3$ to 4×10$^3$ cells were incubated with various numbers of T cells in 200 μl per well of 96-well round-bottom plates in T cell medium, i.e., RPMI 1640 medium, supplemented with 10% FBS and 20 U/ml of IL-2.

In blocking experiments, tumor targets were incubated with various concentrations of anti-HLA or control MAb in 100 μl/well for 1 hour at room temperature before T cells were added. Likewise, T cells were incubated with MAb OKT3 before being transferred to tumor cell-containing wells. Plates were then centrifuged for 3 minutes at 100×g and incubated at 37° C. in a humidified CO$_2$ incubator for 4–6 hours. At the end of the incubation period, plates were spun for 5 minutes at 250×g, supernatants were collected and radioactivity was measured in a γ-counter (Packard, Downers Grove, Ill.). To determine maximum $^{51}$Cr-release, targets were lysed with 0.5 M HCl. To determine spontaneous $^{51}$Cr-release, targets were incubated without effectors. All determinations were performed in triplicate or quadruplicate. The percentage of specific lysis of target cells was determined by the formula: [(Experimental release–spontaneous release)/(Maximum release–spontaneous release)]×100.

A. CTL007 Cells

Figure 4:
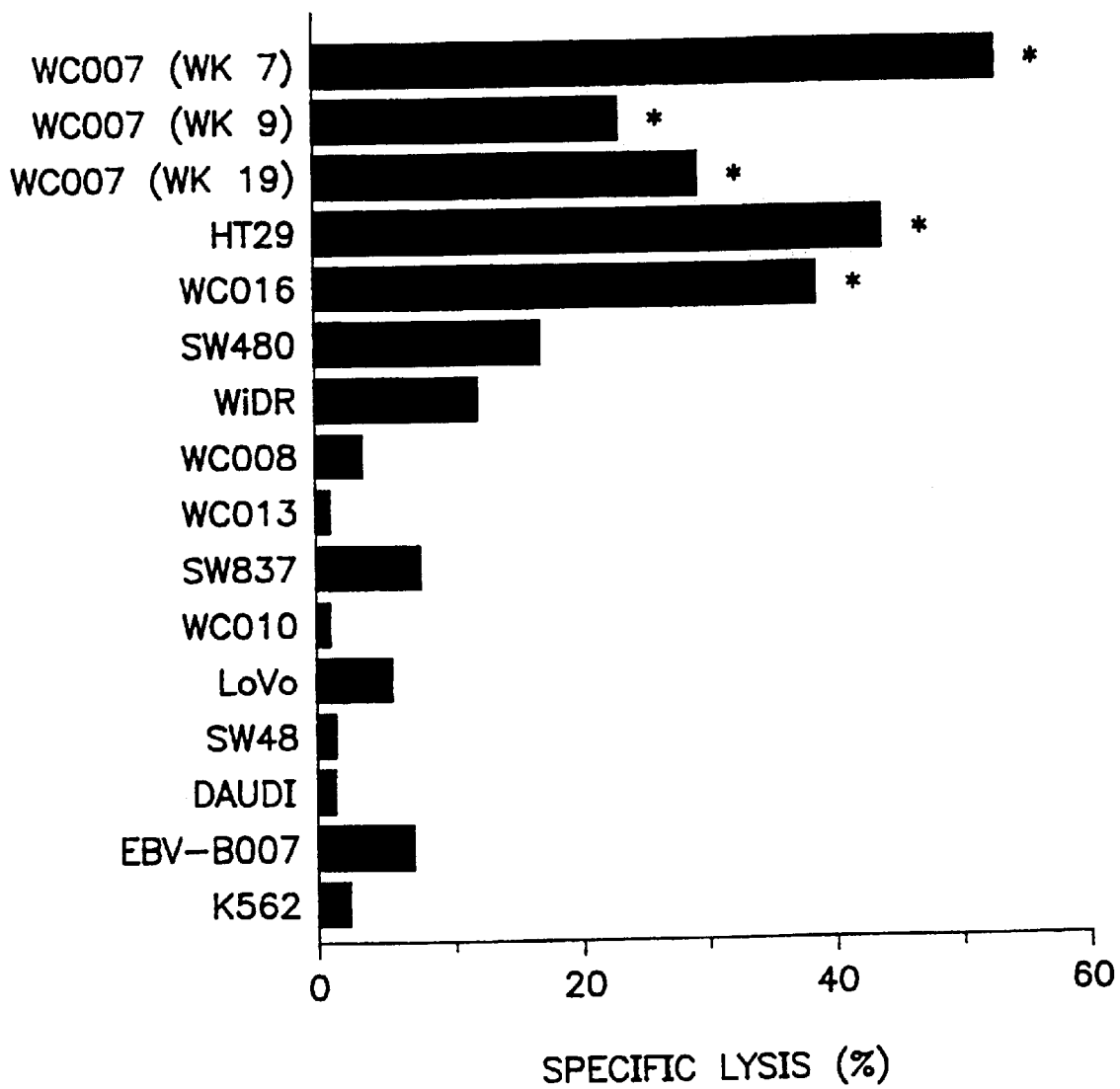
FIG. 4 is a bar graph charting the cytolytic activity of CTL. CTL (7 to 19 weeks in culture, see numbers in parentheses) were tested for cytolytic activity (4–6 hours $^{51}$Cr release assay) against autologous and allogeneic CRC cells, autologous EBV-B cells, K562, and Daudi cells. An asterisk represents the $^{51}$Cr-release in test wells (containing targets plus CTL) which was significantly ($p<0.05$) higher than in control wells (containing target cells in the absence of CTL).
Figure 5A:
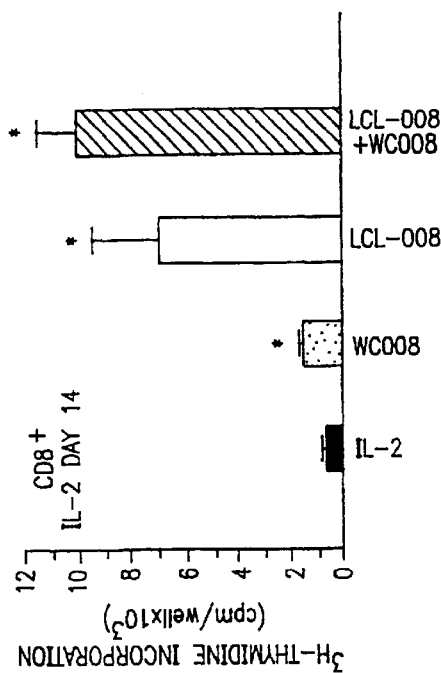
FIG. 5A is a bar graph illustrating proliferative responses of CD8+ CTL008 cells from a different patient (008) described in Example 6. Mixed lymphocyte tumor culture (MLTC) that had received IL-2 from day 8 of culture were sorted into predominantly CD8+ cells on day 36 of MLTC. Sorted lymphocytes ($1 \times 10^4$ cells/well) were cultured in the presence of IL-2 (20 U/ml), autologous WC008 tumor cells ($1 \times 10^3$/well) and/or lymphoblastoid cell line (LCLs; e.g., EBV-B; $5 \times 10^4$/well) for 8 days, and proliferation was measured in [$^3$H] TdR assay. Values are means of triplicate determinations. *$p<0.005$ as compared to T cells grown in IL-2-containing medium only.
Figure 5B:
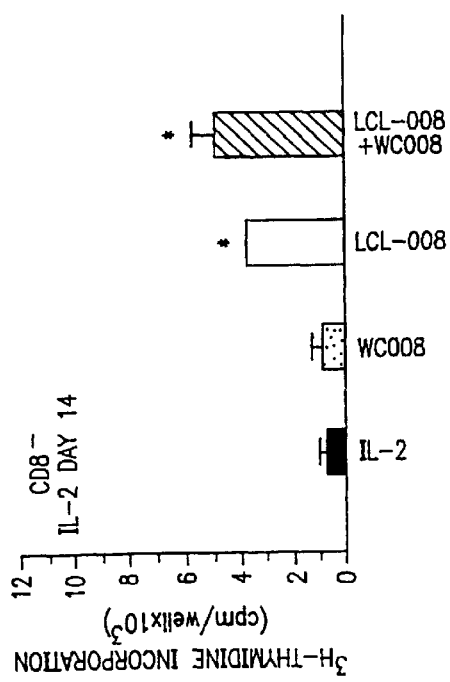
FIG. 5B is a bar graph illustrating proliferative responses of CD8+ T cells. MLTC that had received IL-2 from day 14 of culture were sorted and treated as described in FIG. 5A.
Figure 5C:
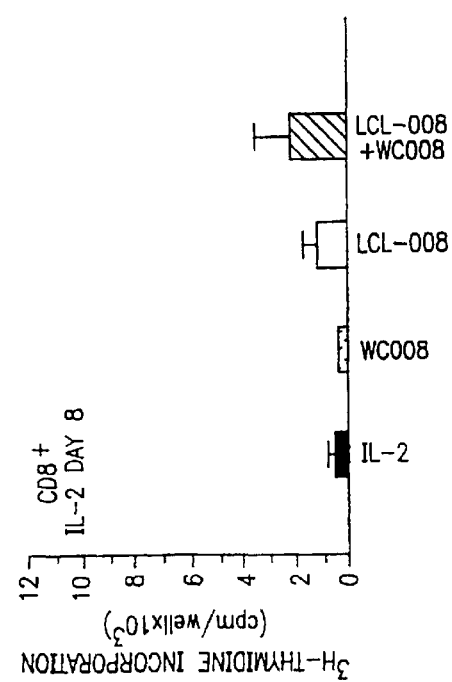
FIG. 5C is a bar graph illustrating proliferative responses of CD8– T cells. MLTC that had received IL-2 from day 8 of culture were sorted into predominantly CD8– cells and otherwise treated as described in FIG. 5A.
Figure 5D:
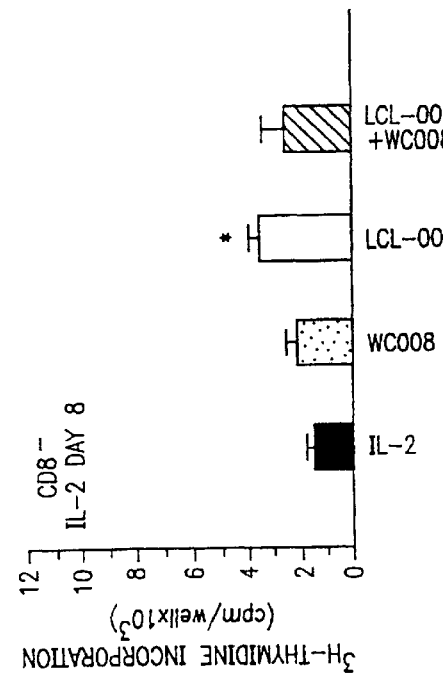
FIG. 5D is a bar graph illustrating proliferative responses of CD8– T cells. MLTC that had received IL-2 from day 14 of culture were treated as described in FIG. 5A.
Figure 6A:
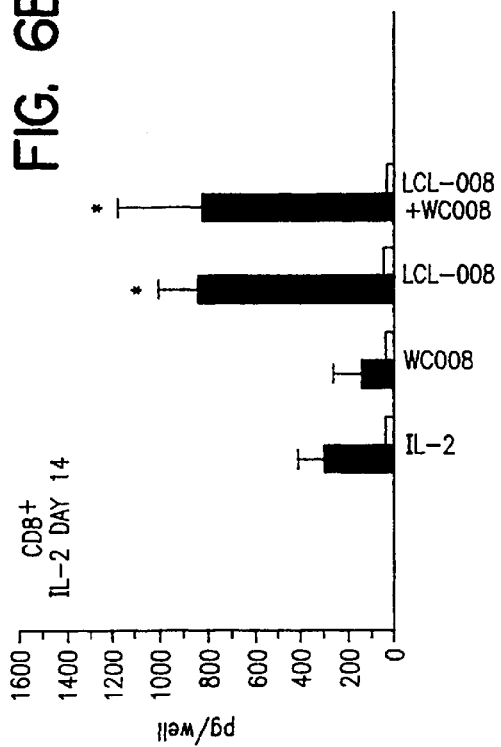
FIG. 6A is a bar graph illustrating Th1-type (WFN-γ, solid columns) and Th2-type (IL-4, open columns) cytokine release of CD8+ sorted MLTC008 cultures (day 46 of MLTC, i.e., day 10 after sort). MLTCs were initiated, sorted and restimulated and cytokine release was determined by radioimmunoassay (RIA). Values are means of triplicate determinations. *$p<0.005$ as compared to T cells grown in IL-2-containing medium only.
Figure 6B:
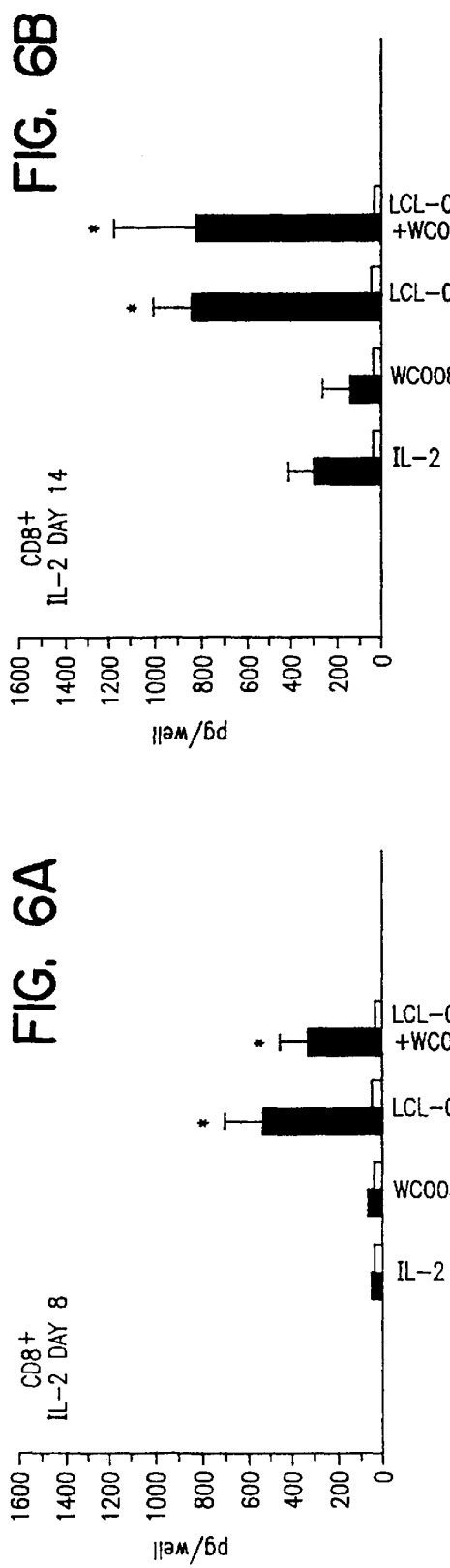
FIG. 6B is a bar graph illustrating Th1-type (IFN-γ, solid columns) and Th2-type (IL-4, open columns) cytokine release of CD8+ sorted MLTC008 cultures which has received IL-2 from day 14 of culture, and were otherwise treated as in FIG. 6A.
Figure 6C:
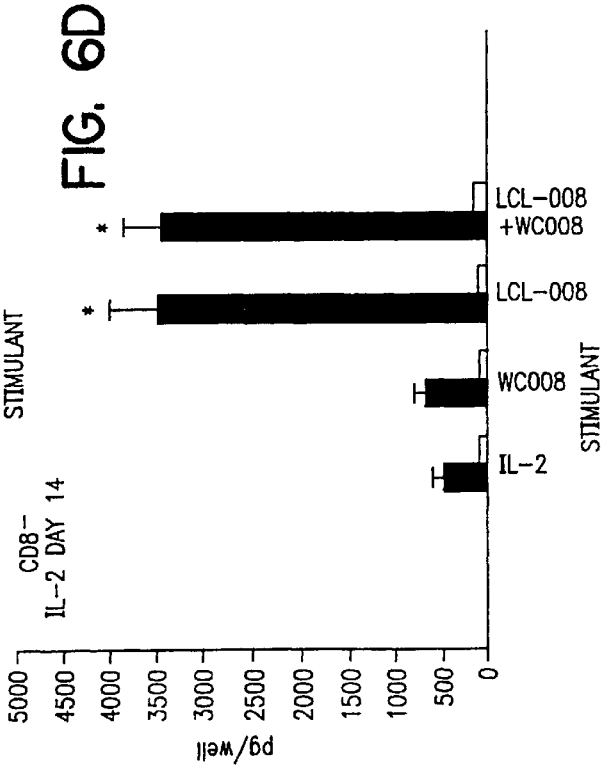
FIG. 6C is a bar graph illustrating Th1-type (IFN-γ, solid columns) and Th2-type (IL-4, open columns) cytokine release of CD8– sorted MLTC008 cultures which has received IL-2 from day 8 of culture, and were otherwise treated as in FIG. 6A.
Figure 6D:
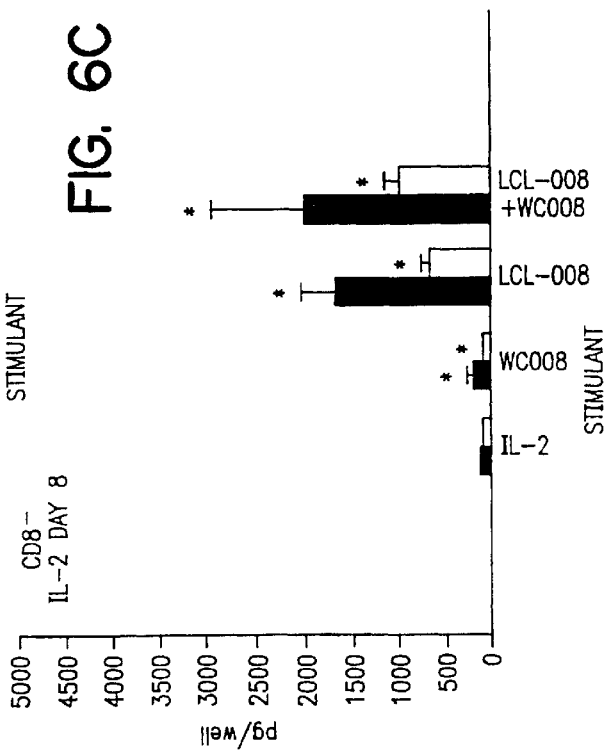
FIG. 6D is a bar graph illustrating Th1-type (IFN-γ, solid columns) and Th2-type (IL-4, open columns) cytokine release of CD8-sorted MLTC008 cultures which have received IL-2 from day 14 of culture, and were otherwise treated as in FIG. 6A.

Analysis of the cytotoxic activity of the CTL007 revealed lysis of autologous WC007 tumor cells in standard 4–6 hours $^{51}$Cr release assays throughout the 19 week culture period of the CTL007 (See FIG. 4). The following Table 5 lists the HLA types matched with or expressed by WC007, and corresponding to the tumor cells tested in FIG. 4. HLA types marked with superscript 1 were expressed by tumor cells only after IFN-γ treatment. Superscript 2 denotes HLA type not yet confirmed for expression by tumor cells. HLA types in bold are matched between WC007 and other cell lines. As can be observed by the results of FIG. 4 and Table 5 below, lytic activity of CTL007 was significantly enhanced by treatment of the tumor cells with IFN-γ (20 U/ml), probably reflecting upregulation of HLA-class I on the tumor cells by the cytokine, since lysis of tumor cells is HLA-class I-dependent. The CTL007 also lysed allogeneic CRC cells WC016 matched for HLA-A3, and HT-29 matched for HLA-A1 (FIG. 4). However, HLA-A1-matched CRC cells WC013 and HLA-A1- and A3-matched CRC cells WC008 were not lysed, presumably because they lack the tumor antigen recognized by the CTL007 or HLA expression is too low for lysis to occur (e.g., WC008 cells express HLA-A1 only after IFN-γ treatment), or these cell lines express HLA-A1 and -A3 subtypes not shared with those of WC007 cells [D. Barouch et al, *J. Exp. Med.*, 182:1847–1856 (1994)].

HLA-nonmatched CRC cells (WC010, WiDR, SW837, SW48, LoVo), K562, Daudi, and autologous EBV-B cells were not lysed by the CTL007 (FIG. 4).

To determine whether CD3 molecule on the CTL007 and HLA-class I or -DR on the target cell are involved in the target recognition by the CTL, $^{51}$Cr-release blocking assays using MAbs to these markers were performed. Lysis of autologous tumor cells was specifically and significantly (p<0.001) blocked by anti-HLA-A, -B, -C MAb W6/32 (up to 83% inhibition) and anti-CD3 MAb OKT3 (up to 95% inhibition). Results of assays using IgM MAb to HLA-A1 or -A3 to block CTL lysis of CRC targets were inconclusive because of high non-specific inhibition of lysis obtained with irrelevant IgM control MAb.

TABLE 5

| Tumor Cells tested in $^{51}$Cr release assays | HLA matched with/expressed by WC007 |
|---|---|
| WC007 (wk 7, 9 and 19) | A1, A3$^1$, B35, Cw4, Cw8, DR$^1$ (DR1, DR4) |
| HT29 | A1, Cw4$^2$, Cw8$^2$, DR$^1$ (DR1$^2$, DR4$^2$) |
| WC016 | A3, DR$^1$ (DR4) |
| SW480 | Cw4$^2$, Cw8$^2$, DR$^1$ (DR1$^2$, DR4$^2$) |
| WiDR | Cw4$^2$, Cw8$^2$, DR1$^2$, DR4$^2$ |
| WC008 | A1$^1$, A3, DR4 |
| WC013 | A1, Cw4 |
| SW837 | B35$^2$, Cw4$^2$, Cw8$^2$, DR$^1$ (DR1$^1$, DR4$^2$) |
| WC010 | none |
| LoVo | none |
| SW48 | none |
| Daudi | none |
| EBV-B007 | A1$^1$, A3$^1$, B35, Cw4$^1$, Cw8$^1$, DR$^1$ (DR1, DR4) |
| K562 | none |

B CTL008

Figure 8:
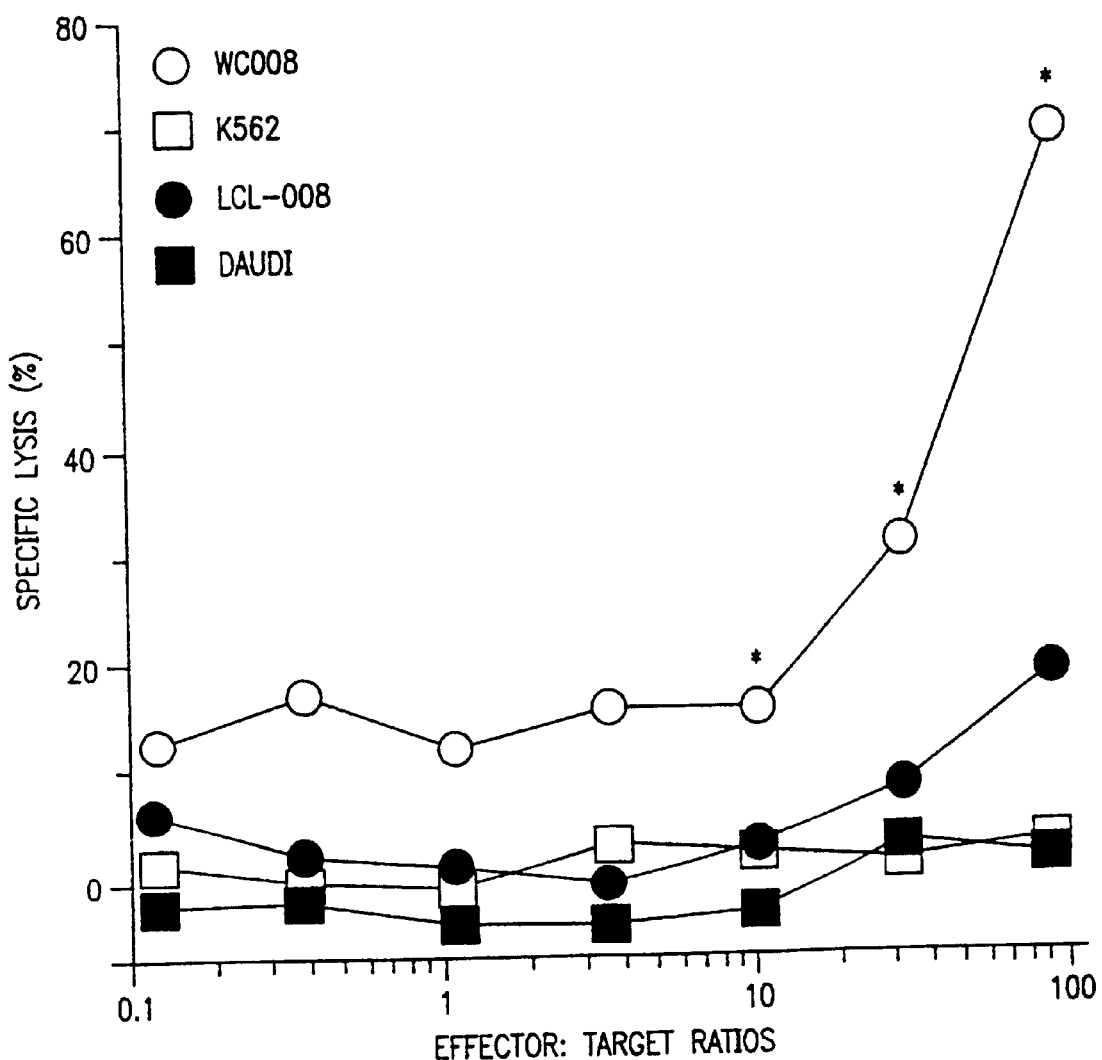
FIG. 8 is a graph illustrating cytolytic response of the predominantly CD8+-sorted T-cell line CTL008 (IL-2 from day 14 of MLTC) on day 84 of MLTC, i.e. 48 days after sort. Lysis of autologous tumor cells, WC008 (○) and LCL cells, LCL-008 (●) cells, NK target cells, K562 (□) or lymphokine-activated killer (LAK) target cells, Daudi (■) was measured in a 6-hour $^{51}$Cr-release assay. "*" represents that the mean cpm (triplicate determinations) were significantly (p<0.05) higher than the mean cpm of control values (spontaneous $^{51}$Cr-release of target cells).

Analysis of the cytotoxic activities of the CD8$^+$ and CD8$^-$ $_{CTL}$008 T-cell lines (day 8 or 14 IL-2) against various target cells 14 days after the sort (FIGS. 7A–7B) showed that only the CD8$^+$ T-cell line cultured with IL-2 from day 14 of MLTC lysed the autologous tumor cells at significant levels. However, tumor lysis was low (approximately 8%). In addition, this line also lysed NK target cell K562, but not autologous LCLs (FIGS. 7A–7B). However, at 48 days after the sort (84 days in culture), when the culture had reverted to a predominantly CD4$^+$ phenotype (Table 4), the CTL line showed high lytic activity (>65% lysis) directed exclusively against the autologous tumor cells (FIG. 8). Seventy-eight days after the sort (day 114 in culture), the CTL line still showed significant lysis of autologous WC008 cells, but did not lyse HLA class I antigen-nonmatched CRC cells SW48 and LS180, partially HLA class I antigen-matched CRC cells SW837 (matched for HLA-B62[15]) or SW480 (matched for HLA-B57[17])CRC cells (Table 6).

Table 6 shows the absence of lysis of partially HLA-matched or HLA-nonmatched CRC cell lines by CTL008 (day 114 of MLTC). Lysis was determined in a 6-hour $^{51}$Cr-release assay at an effector-to-target ratio of 40:1.

TABLE 6

| CRC target cell line | HLA-matched with or expressed by WC008 cells | Specific lysis (%) |
|---|---|---|
| WC008 | A1, $^1$A3, B57[17], B62[15 | 27.5$^2$ |
| SW48 | none | −5.8 |
| LS180 | none | 3.9 |
| SW837 | B62[15] | 4.6 |
| SW480 | B57[17] | 4.8 |

$^1$HLA-A1 was detectable only after treatment of the cells with IFN-γ.
$^2$Values are means of quadruplicate determinations. p = 0.03 vs. control (in the absence of effector cells).

Figure 9:
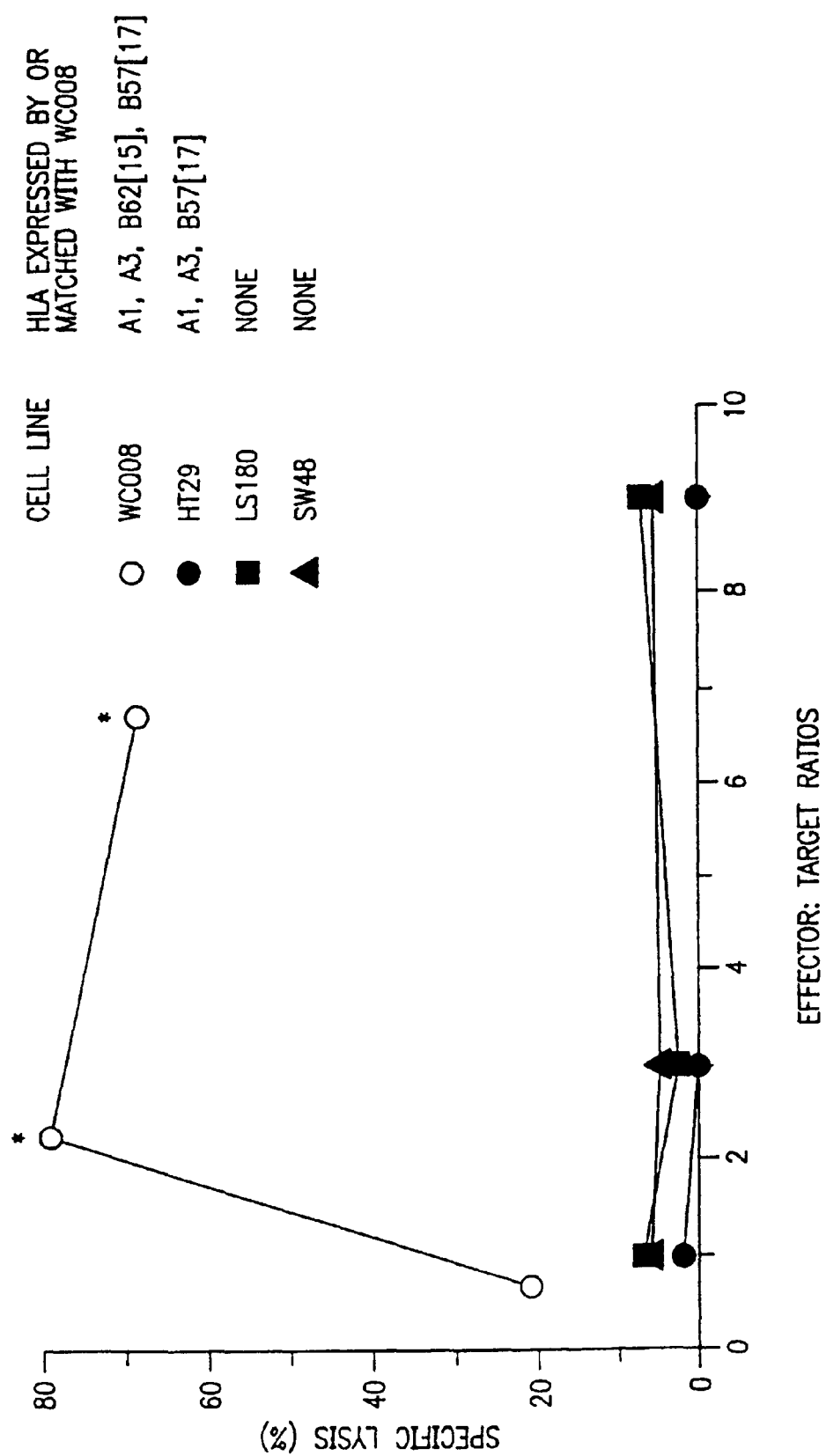
FIG. 9 is a graph illustrating lysis of autologous CRC cells, but not partially HLA-matched or nonmatched allogeneic CRC cells by CTL008cl.C2 (98 days in culture). Target cells used in a 6-hour $^{51}$Cr-release assay were: WC008 autologous CRC cells (HLA-A1 was detectable only after treatment of the cells with IFN-γ) (○); HT-29 allogeneic CRC cells matched for HLA-A1, -A3 and -B57 [17] (●), LS180 (■), and SW48 (▲) HLA-nonmatched allogeneic CRC cells. "*" indicates that the mean cpm (triplicate determinations) were significantly (p<0.0005) higher than mean cpm of control values (spontaneous $^{51}$Cr-release of target cells.)

CTL008 clone (98 days in culture) lysed up to 80% of autologous WC008 tumor cells at an effector-to-target ratio of 2.2:1, whereas allogeneic CRC cells SW48 and LS180, both HLA nonmatched with WC008 cells, and HT-29, matched for HLA-A1, -A3 and -B57[17], were not lysed (FIG. 9).

EXAMPLE 8

Cytokine Determinations

Cell-free supernatants (48 hours) of T-cell lines stimulated with autologous tumor cells in the presence of autologous irradiated EBV-B and in the absence (IL-2 determinations) or presence (IFN-γ, IL-4, and TNF-α determinations) of IL-2 (20 U/ml) were tested for cytokine activities as previously described [R. Somasundaram et al, cited above].

IL-2 was measured in diluted supernatants in a bioassay using the IL-2-dependent murine T-cell line CTLL-2 (obtained from W. Gerhard, The Wistar Institute). CTLL-2 cells ($1 \times 10^4$ cells/flat-bottom microtiter well) were incubated for 48 hours with diluted supernatants, pulsed with $^3$H-thymidine for the last 18 hours of incubation, and assessed for $^3$H-thyridine incorporation. IL-2 concentrations were determined using IL-2 standards (Boehringer Mannheim).

IFN-γ was measured in radioimmunoassay (RIA). Microtiter plates (Microlite TM, Dynatech, Chantilly, Va.) were coated overnight at 4° C. with 0.5 μg/well of purified FN-γ-specific MAb B133.1.1. Plates were then washed, blocked and incubated with 100 μl/well of sample or standard IFN-γ in T cell media containing IL-2 (20 U/ml) [IFN Sciences, New Brunswick, N.J.] overnight at 4° C. Plates were again washed and incubated overnight with 0.01 μg/well of $^{125}$I-labeled IFN-γ specific MAb B133.5.1, which binds to a different determinant than that recognized by MAb B133.1.1 (in phosphate buffered, saline PBS containing 5% FBS and 0.05% TWEEN 20 buffer). Plates were washed and counted in a microplate γ-scintillation counter (Packard).

IL-4 and TNF-α were measured in RIA essentially as described for IFN-γ. Anti-IL-4 MAb 4F2 was used as coating antibody and $^{125}$I-labeled MAb B154.7.1 to a different determinant on TNF-α or similarly labeled MAb 5AG to a different determinant on IL-4 as tracer. Recombinant human IL-4 (Genzyme, Cambridge, Mass.) and TNF-α (Chiron, San Diego, Calif.) were used as standards. All cytokine determinations were done in triplicate or quadruplicate.

A. CTL007

CTL007 produced low, but significant amounts of IL-2 (up to 3 U/ml), even if cultured without tumor cells and EBV-B cells for 2 days. The CTL007 also produced significant amounts of IFN-γ (up to 25.6 U/ml) when cultured with either autologous EBV-B cells or both tumor and EBV-B cells for 2 days, but not when cultured with tumor cells alone. CTL007 produced IL-4 (up to 14.5 U/ml) under all culture conditions used.

B. CTL008

All four sorted WC008 lymphocyte cultures (CD8+, day 8 IL-2; CD8+, day 14 IL-2; CD8−, day 8 IL-2; CD8− day 14 IL-2) produced significant amounts of IFNγ (Th1-type cytokine secretion pattern) (Mosman et al, 1986) when stimulated with either autologous EBV-B cells (LCLs)or both autologous EBV-B cells and tumor cells (FIGS. 6A–6D). Stimulation with tumor cells alone induced low, but significant IFN-γ secretion in only one line (CD8−, day 8 IL-2), and only this line produced significant amounts of IL-4 (Th2-type cytokine secretion pattern; Parronchi et al., 1991) after stimulation with autologous tumor cells, LCLs alone or LCLs in combination with tumor cells (FIGS. 6A–6D).

EXAMPLE 9

Flow Cytometry

Cells were washed, plated into wells of 96-well plates ($1 \times 10^5$ cells/well/50 μl cold FACS medium: RPM1 1640 medium supplemented with 2% human AB serum and 0.02% NaN$_3$) and incubated with saturating concentrations of unlabeled MAb (indirect immunofluorescence test), or FITC- or phycoerythrin (PE)-labeled MAb (direct fluorescence test) for 30 minutes at 4° C. Cells were then washed 2 or 3 times in cold FACS medium and either directly analyzed (direct immunofluorescence test) or incubated with FITC-labeled goat IgG specific for mouse IgG F(ab')$_2$ (Cappel Labs, West Chester, Pa.), FITC-labeled donkey anti-mouse IgM antibody (Jackson, West Grove, Pa.), or FITC-labeled goat anti-human IgM antibody (Sigma), all at a 1:200 final dilution, for an additional 30 minutes, before being washed again (indirect immunofluorescence test). Samples were analyzed in the cytofluorograph (Ortho Diagnostics, Raritan, N.J.) or EPICS ELITE flow cytometer (Coulter Corporation, Hialeah, Fla.). All values given are corrected for binding of irrelevant isotype-matched control antibody.

Results of this examples are reported in Tables 3 and 4 above.

EXAMPLE 10

Reverse Transcriptase-PCR Amplification and Analyses of TCR VA and VB Gene Segments T-cell lines (e.g., CTL007 cell lines: 17 weeks in culture; CTL008: day 208 of MLTC; and T-cell clone CTL008cl.C2: day 122 after cloning) were purified using anti-CD4 MAb-coated magnetic beads (Dynal, Oslo, Norway) to eliminate potential contamination of feeder cells. Poly A+ mRNA was isolated using a kit employing oligo-dT coated magnetic beads according to the manufacturer's instructions (Dynal).

Briefly, MRNA from lysates of between $1–4 \times 10^4$ to $2 \times 10^6$ T cells was annealed to 64 μg oligo-dT coated beads (or to 30 μl of these beads at about 5 mg/ml) for 5 minutes at room temperature. Beads were then washed and resuspended in 10–30 μl of water. Solid-phase, oligo-dT-primed cDNA was then generated by incubating 2–8 μl of beads with 200 U RNASIN reagent (Promega, Madison, Wis.), 0.5 mM each of dATP, dCTP, dGTP, and dTTP (Boehringer Mannheim), 10 mM DTT, and 800 U SUPERSCRIPT reverse transcriptase (Gibco BRL, Baltimore, Md.) in a total volume of 80 to 800 μl for 60 minutes at 37° C. The reaction was stopped by incubation at between 90–98° C. for 2 minutes. cDNA covalently bound to the bead surface was washed twice and resuspended in 200 μl of water or in 50 μl TE buffer. Amplification of cDNA by PCR was carried out for 35 cycles in 25 μl reaction volumes (0.5 μl solid phase cDNA per reaction) using Taq polymerase (Boehringer Mannheim, 1 U/reaction) and primers derived from TCR Vα and Vβ primer kits (Clontech, Palo Alto, Calif.), according to the manufacturer's instructions. The kits provided 5' primers specific for 22 Vα and 25 Vβ region genes and one 3' primer each specific for Cα or Cβ regions.

Figure 3:
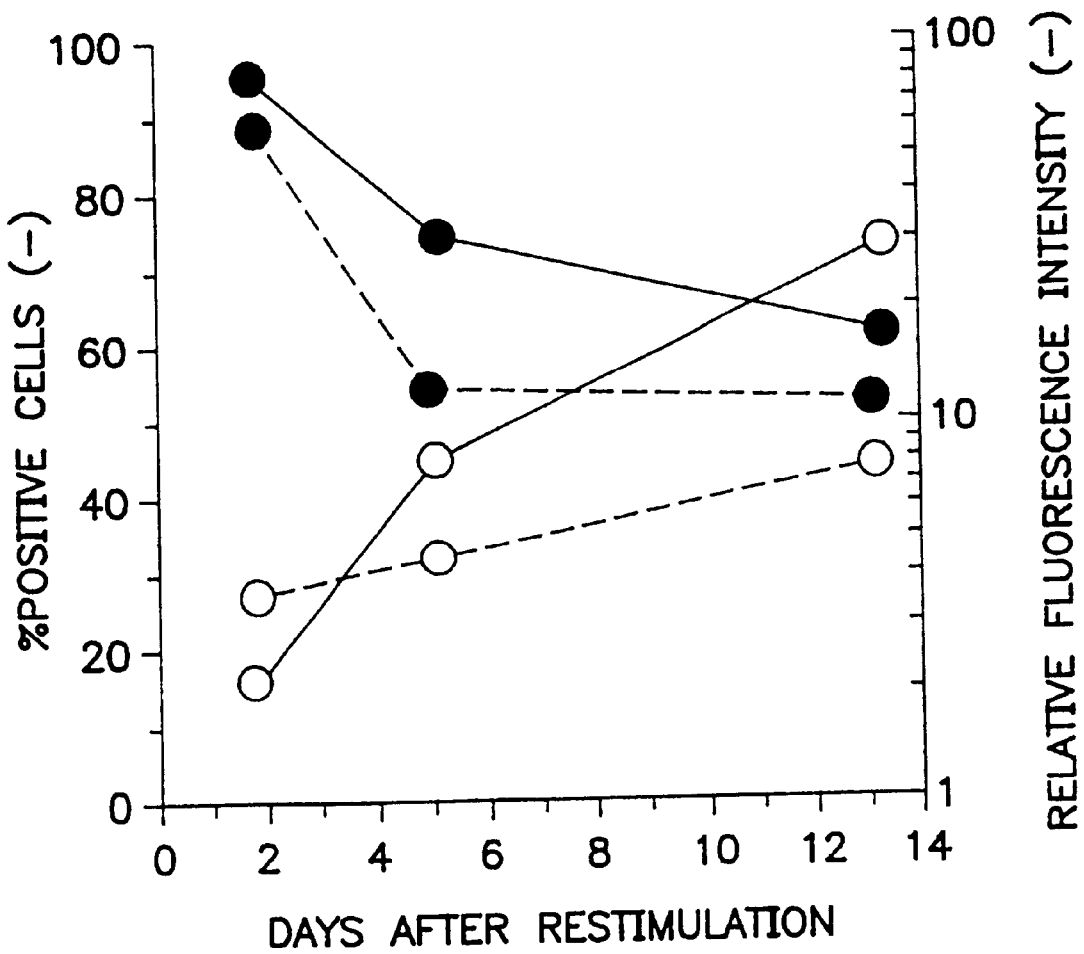
FIG. 3 is a graph depicting the kinetics of HLA-DR and TCR Vβ12 expression by the CTL cell line. T cells (17 to 19 weeks in culture) were stimulated with autologous WC007 CRC and EBV-B cells on day 0. HLA-DR (●) and TCRVβ12 (○) expression were measured by direct immunofluorescence analysis on days 2, 5, and 13. Solid lines represent percent of positive cells; dotted lines represent relative mean fluorescence intensity, corrected for irrelevant monoclonal antibody (MAb) binding.

The CTL007 line expressed three major TCR Vα transcripts (Vα 8, 11, and 20) and only one major Vβ transcript (Vβ 12) as determined by RT-PCR in week 17 of MLTC. Thus, the CTL line most likely is not of clonal origin. TCR Vβ12 expression increased with time after restimulation of the CTL007 with autologous tumor and EBV-B cells, whereas expression of the activation marker HLA-DR significantly decreased with increasing time after CTL stimulation (FIG. 3).

TCR analysis of the CD8+-sorted CTL008 cells (day 14 IL-2) revealed strong expression of Vα5, Vβ36 and Vβ14 genes, and weak expression of Vα11 and Vα14 genes.

The CTL008 clone expressed 2 TCR Vα transcripts (Vα11 and 22) and one Vβ transcript (Vβ14) as demonstrated by RT-PCR, Thus, the CTL008 cells most likely are of clonal origin [Padovan, E., et al., Science, 262: 422–425 (1993)].

All above-referenced published documents are incorporated by reference herein. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:
1. A cell line CTL007 ATCC Accession No. CRL12518.
2. A composition comprising a cell line of claim 1 in a suitable carrier.

* * * * *

UNITED STATES PATENT AND TRADEMARK OFFICE
Certificate

Patent No. 6,528,307                                         Patented: March 4, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Dorothee Herlyn, Wynnewood, PA; Lutz Jacob, Yarraville, Australia; and Rajasekharan Somasundaram, West Chester, PA.

Signed and Sealed this Twenty-seventh Day of January 2004.

<div align="right">
CHRISTINA CHAN<br>
<i>Supervisory Patent Examiner</i><br>
Art Unit 1644
</div>